(12) United States Patent
Coppens

(10) Patent No.: US 8,980,945 B2
(45) Date of Patent: Mar. 17, 2015

(54) VIRAL INHIBITOR COMPOSITIONS FOR IN VIVO THERAPEUTIC USE COMPRISING A COMBINATION OF (−)-CARVONE, GERANIOL AND A FURTHER ESSENTIAL OIL COMPONENT

(75) Inventor: Christine Coppens, Strassen (LU)

(73) Assignee: Cessa Alliance, Strassen (LU)

( * ) Notice: Subject to any disclaimer, the term of this patent is extended or adjusted under 35 U.S.C. 154(b) by 0 days.

(21) Appl. No.: 13/582,784

(22) PCT Filed: Mar. 28, 2011

(86) PCT No.: PCT/EP2011/054758
§ 371 (c)(1),
(2), (4) Date: Sep. 5, 2012

(87) PCT Pub. No.: WO2011/117424
PCT Pub. Date: Sep. 29, 2011

(65) Prior Publication Data
US 2013/0225676 A1    Aug. 29, 2013

(30) Foreign Application Priority Data
Mar. 26, 2010 (EP) ..................... 10157930

(51) Int. Cl.
*A61K 31/045* (2006.01)
*A61K 31/122* (2006.01)
*A61K 31/085* (2006.01)
*A61K 31/336* (2006.01)

(52) U.S. Cl.
CPC ............. *A61K 31/122* (2013.01); *A61K 31/045* (2013.01); *A61K 31/085* (2013.01); *A61K 31/336* (2013.01)
USPC .......................................... 514/475; 514/690

(58) Field of Classification Search
CPC . A61K 31/045; A61K 31/122; A61K 31/336; A61K 31/085
USPC .................................................. 514/475, 690
See application file for complete search history.

(56) References Cited

U.S. PATENT DOCUMENTS

| | | | | |
|---|---|---|---|---|
| 4,902,678 | A | * | 2/1990 | Smith ............................. 514/45 |
| 5,856,364 | A | * | 1/1999 | Martin .......................... 514/724 |
| 6,121,234 | A | * | 9/2000 | Benet et al. .................. 514/20.5 |
| 2004/0071757 | A1 | * | 4/2004 | Rolf .............................. 424/443 |

FOREIGN PATENT DOCUMENTS

WO    WO 02/056879    *    7/2002

OTHER PUBLICATIONS

Bassat et al. Flavour and Fragrance Journal, (1987) vol. 2, 95-97.*
Leonardo et al. J. Phys. Chem. A 2010, 114, 5468-5477.*
Park et al., Fitoterapia 80 (2009) 290-296.*

* cited by examiner

*Primary Examiner* — Savitha Rao
*Assistant Examiner* — Angela Brown-Pettigrew
(74) *Attorney, Agent, or Firm* — Fish & Tsang, LLP

(57) ABSTRACT

The present invention concerns an antiviral composition comprising the following components: R-(−)-2-methyl-5-(prop-1-en-2-yl)-cyclohex-2-enone (also called (−) carvone) and S-(+)-2-methyl-5-(prop-1-en-2-yl)-cyclohex-2-enone (also called (+) carvone) and (2E)-3,7-dimethylocta-2,6-dien-1-ol (also called trans-geraniol) in combination with at least one more component chosen among essential oils components for use in treatment and prevention of diseases caused by DNA enveloped viruses, DNA non-enveloped viruses, RNA enveloped viruses and RNA non-enveloped viruses.

5 Claims, No Drawings

VIRAL INHIBITOR COMPOSITIONS FOR IN VIVO THERAPEUTIC USE COMPRISING A COMBINATION OF (−)-CARVONE, GERANIOL AND A FURTHER ESSENTIAL OIL COMPONENT

FIELD OF THE INVENTION

The present invention relates to the pharmaceutical field. The man skilled in the art can be a virologist.

The present invention relates to a composition for use in treatment and prevention of diseases caused by DNA enveloped, DNA non-enveloped, RNA enveloped, RNA non-enveloped virus, use of the composition as a prophylactic, use of the composition as a disinfectant, use of the composition as a viral inhibitor.

BACKGROUND OF INVENTION

U.S. Pat. No. 4,402,950 is considered as the closest prior art as it discloses (in vitro) the antiviral activity of carvone against adenovirus type 6, which is a double stranded DNA non enveloped virus.

U.S. Pat. No. 4,402,950 discloses in its claim 1 "a process for deactivating viruses inside living human and animal organisms infected with said viruses comprising administering to one of said organisms a terpene selected from the group consisting of black pepper oil, cinnamon flower oil, cardamon oil, linallyl acetate, cinnamic aldehyde, carvone, and cis/trans citral, in a dosage amount effective to deactivate said viruses but ineffective to cause toxic effects on living cells of the living organism."

The first column of U.S. Pat. No. 4,402,950 mentions at line 61 that the carvone used is from the fruit of *Carum carvi*. The man skilled in the art will therefore easily deduct that the carvon used in U.S. Pat. No. 4,402,950 is the enantiomer "(+)-carvon". In fact it is well known in the literature that S-(+)-Carvone is the principal constituent of the oil from caraway seeds (*Carum carvi*).

The difference between the present invention and the closest prior art is:
a composition comprising R-(−)-2-methyl-5-(prop-1-en-2-yl)-cyclohex-2-enone (also called (−)-carvon) and (2E)-3,7-dimethylocta-2,6-dien-1-ol (also called trans-geraniol) in combination with at least one more component chosen among essential oils in a pharmaceutically effective concentration (see list D which is disclosed in the present invention) for use in treatment and prevention of diseases caused by DNA enveloped viruses, DNA non-enveloped viruses, RNA enveloped viruses and RNA non-enveloped viruses, said diseases are those mentioned in claim 1.

The technical effect of the above mentioned difference is that an unexpected and surprising regression of lesions on the surface of the cervix occurred, in vivo (between 20%-100%: see the comparative tests), while there is no medical effect occurring when any individual component is tested alone in vivo.

The objective technical problem to be solved is considered as the provision of a synergetic (alternative) antiviral composition comprising (+) carvone having an antiviral effect.

The question to be answered now is whether there is any teaching in the prior art as a whole (like U.S. Pat. No. 3,429,971) that would have prompted the skilled person, faced with the objective technical problem, to modify the closest prior art while taking account of that teaching, thereby arriving at something falling within the terms of the claims, and thus achieving what the invention achieves. The answer to this question is clearly NO. We explain why as follows:

U.S. Pat. No. 3,429,971 discloses a method of treating avian lymphomatosis induced by ES strain of lymphomatosis virus which comprises administering to a bird an effective amount of Cis-Geraniol. It is well known from a man skilled in the art that the isomers Cis-Geraniol and Trans-Geraniol have different biological/biochemical properties. This is even proved in U.S. Pat. No. 3,429,971:

The skilled person would never have combined U.S. Pat. No. 4,402,950 with U.S. Pat. No. 3,429,971 because U.S. Pat. No. 3,429,971 discloses in column 3, table 2 second and third rows:

"Trans-2,6-dimethyl-2,6,octadiene-8-ol->No. cures: 0".

Trans-2,6-dimethyl-2,6,octadiene-8-ol corresponds to the component "Trans-geraniol, i.e. to (2E)-3,7-dimethylocta-2,6-dien-1-ol".

The virus mentioned in U.S. Pat. No. 3,429,971 is the avian lymphomatosis virus, which is a double stranded DNA enveloped virus (herpesviridae family).

The man skilled in the art, starting from U.S. Pat. No. 4,402,950 would be led to search a second component deactivating a virus of the same family as U.S. Pat. No. 4,402,950, i.e. a DNA non enveloped virus and therefore would not be led to search a further component deactivating a DNA enveloped virus. Even, if the man skilled in the art would be aware of the existence of U.S. Pat. No. 3,429,971, he would never use the component Trans-Geraniol in combination with carvone because column 3, table 2 second and third rows of U.S. Pat. No. 3,429,971 would dissuade him to combine both components because the man skilled in the art will learn that Trans-Geraniol does not have any curing effect (see table 2 of U.S. Pat. No. 3,429,971, namely the value zero cure).

In addition, the man skilled in the art would never find any indication in the prior art giving him any hint to use a composition containing carvone and Trans-Geraniol combined with at least one more component chosen among essential oils in a pharmaceutically effective concentration and selected from the list of components of claim 2 because the components listed in claim 2 are nor disclosed in U.S. Pat. No. 4,402,950, nor in U.S. Pat. No. 3,429,971, in combination.

The comparative tests listed in the present invention prove the above assertion. Even if the man skilled in the art would have, for an unknown reason, combined carvone with Trans-Geraniol for deactivating a DNA non enveloped virus, the comparative tests prove that no regression of lesions on the surface of the cervix have been observed, while for the synergetic composition of claim 1, 20%-100% of regression of lesions on the surface of the cervix have been observed. Consequently, there is a synergism between the combination of (+) carvone and (−) carvone and Trans-Geraniol and at least one more component chosen among essential oils in a pharmaceutically effective concentration of the present invention provoking an unexpected and surprising effect, i.e. 20%-100% of regression of lesions on the surface of the cervix.

Clinical and experimental pharmacology and physiology (2005) 32, pages 811-816 entitled "antiviral activities of extracts and selected pure constituents of *ocimum basilicum*" shows that purified components of *ocimum basilicum* were used to identify possible antiviral activities against human DNA viruses (HSV, ADV) and RNA viruses (CVB1, EV71). No activity was noted for carvone, cineole, beta-caryophylene, farnesol, fenchone, geraniol, beta-myrcene and alpha-thujone (it is to understand that no activity was noted for each component used alone). The difference between the present invention and this document is that the composition of the present invention is a synergetic combination of several compounds which proved having an unexpected antiviral effect.

Antiviral research 42 (1999) pages 219-226 is entitled "plant products as topical microbicide candidates: assessment of in vitro and in vivo activity against herpes simplex virus type 2" relates to protective efficacy in vivo in a mouse (see page 220 second column last paragraph) and a guinea pig model (see page 223 second column) of genital HSV-2 infection. At page 223 second column it is mentioned that infection in a guinea pig model, unlike in the mouse, does not result in death and more closely mimics the natural course of disease in humans. For these experiments, 0.1 ml of eugenol was instilled into the vaginal vault of female guinea pigs followed 20 seconds later by instillation of 0.1 ml of virus suspension containing $10^6$ pfu of HSV-2 MS strain. Table 2 shows that treatment with eugenol immediately prior to intravaginal inoculation resulted in significant fewer animals developing symptomatic primary disease compared to PBS-treated controls. These data indicate that eugenol does have direct antiviral activity. The difference between the present invention and "Antiviral research 42 (1999) pages 219-226" is that in the present invention the novel synergetic composition is instilled after the viruses infected the human body in order to treat human diseases. It is obvious for a man skilled in the art that eugenol can be used as a prophylactic in vivo if it is instilled in a dosis of 0.1 ml prior to instillation of 0.1 ml of HSV-2 MS strain suspension in the vagina. The operating steps in the present invention are inversed comparing to those mentioned in the prior art document "Antiviral research 42 (1999) pages 219-226". In addition, Eugenol in the present invention has the chemical formula "2-methoxy-4-prop-2-enylphenol" while page 223 first column second paragraph mentions eugenol as having the formula "4-hydroxy-3-methoxy-allylbenzene" which might be a different structural formula than that of the present invention.

Phytotherapy research 14, pages 495-500 (2000) entitled "In vitro and in vivo activity of Eugenol on human herpesvirus" mentions that Eugenol-acyclovir combinations synergistically inhibited herpesvirus replication in vitro and that topical application of eugenol delayed the development of herpesvirus induced keratitis in a mouse. Eugenol in the present invention has the chemical formula "2-methoxy-4-prop-2-enylphenol", while in the abstract of this document eugenol is mentioned as having the formula "4-hydroxy-3-methoxy-allylbenzene" which might be a different structural formula than that of the present invention. The difference between the present invention and this document is that the composition of the present invention is a synergetic combination of several different compounds (other than the combination Eugenol-acyclovir) which proved having an unexpected antiviral effect. In addition, page 497 second column last paragraph bridging with page 498 first column first paragraph discloses that different dilutions of eugenol were instilled in each eye of mice before virus inoculation; after infection mice received the corresponding treatment three times a day and during 5 days (i.e. 15 applications). The difference between the present invention and this document is that in the present invention the novel synergetic composition is instilled after the viruses infected the human body in order to treat human diseases. The operating steps in the present invention are inversed comparing to those mentioned in this prior art document. It is obvious for a man skilled in the art that eugenol can be used as a prophylactic in vivo if it is instilled in a dosis of 1 mg/ml or 0.5 mg/ml prior to virus inoculation.

Natural Product Communications, 2008 vol. 3, No 7, 1085-1088 entitled "investigation of anticancer and antiviral properties of selected aroma samples" discloses that synthetic nerolidol samples at concentrations less than 5 microMolar have anti-tumor effects in vitro. Antiviral studies were performed to investigate inhibitory effects of the compounds on mouse polyomavirus (MPyV) propagation in 3T6 cells. 3T6 cells were washed with DMEM and incubated with virus inoculum for 1 h at 37° C. After that, DMEM supplemented with FBS and containing compounds to be analyzed was added. The difference between the present invention and this document is that the composition of the present invention is a synergetic combination of several different compounds which proved having an unexpected antiviral effect on humans. Results of tests on human beings cannot be compared to in vitro tests.

General Comments on the Prior Art Documents:

Any prior art document dealing with in vitro tests cannot be considered pertinent because the compositions of the present invention have been tested in vivo i.e. on animals or on human beings and it is well known by a man skilled in the art that test results can strongly differ if they are performed in an in vitro versus an in vivo environment. An extensive literature search did not find out any evidence or correlation that even if a composition is active in vitro, a man skilled in the art could deduct that the same composition would also be active in vivo. We also refer to Antiviral research 42 (1999) pages 219-226 is entitled "plant products as topical microbicide candidates: assessment of in vitro and in vivo activity against herpes simplex virus type 2" (already previously mentioned) where it is stated at page 224 first column "Several compounds showed activity in vitro but performed poorly in vivo. This failure of in vitro results to predict in vivo efficacy has previously been noted by zeitlin et al. (1997)". This is even proven in the table of this document.

SUMMARY OF THE INVENTION

Compositions for use in treatment and prevention of diseases caused by DNA enveloped, DNA non-enveloped, RNA enveloped, RNA non-enveloped viruses are presented.

The technical effect of the present invention is to prevent viruses merging with the host cell(s) by interfering with the viral lipid envelope.

The technical problem to be solved is to prevent the multiplication of the viruses in animals and human beings and therefore curing diseased animals or human beings.

To solve the problem, the present invention provides a synergetic composition according to the claims.

It is inferred from some scientific studies that non-enveloped viruses acquire a lipid envelope from the host and as the composition of the present invention interferes with this triglyceride envelope and the envelope of enveloped viruses, it can be declared that the composition of the present invention will de-activate all types of viruses in vivo within animals or human beings.

Following are the most common viruses that can be deactivated with the compositions according to the present invention.

As the mode of action of the invention is non-specific, the virus species and serotype is irrelevant.

The person skilled in the art knows that all viruses are classified into 4 major groups consisting of DNA enveloped viruses, DNA non-enveloped viruses, RNA enveloped viruses and RNA non-enveloped viruses.

All compositions of the present invention are pharmaceutical compositions in a pharmaceutically effective weight percentage which can treat animal and/or human diseases.

List of Diseases: List E:

The compositions of the present invention are used for treating and preventing a disease related to one of the above mentioned viral groups as well as on diseases selected from the non exhaustive group consisting in: (broncho)-pneumonia, 3 day fever exanthema, acute and chronic hepatitis, acute fever, acute gastroenteritis caused by strains such as Desert Shield Lordsdale Mexico Norwalk Hawaii Snow Mountain Southampton virus, acute gastroenteritis caused by strains such as Houston/86 Houston/90 London 29845 Manchester Parkville Sapporo virus, acute hepatitis, acute respiratory distress syndrome, AIDS, anogenital mucosa, Argentine hemorrhagic fever, arthralgia, avian flu, Bolivian hemorrhagic fever, Brazilian hemorrhagic fever, chickenpox, chronic hepatitis, coma, common cold infection, common cold symptoms, congenital infection, conjunctivitis, contagious ecthyma, contagious pustular dermatitis, cornea, Creutzfeldt-Jakob-Disease, cryptic enteric infection, cytomegaloviral mononucleosis, dengue hemorrhagic fever (DHF), dengue shock syndrome (DSS), diarrhea, eczema, eczema herpaticum, encephalitis, encephalopathy, enteritis, epidemic nephropathy, epidemic polyarthritis and exanthema, epidermodysplasia veruciformis, Epstein-Barr virus infection, exanthema, exanthema in children, Fatal familial insomnia, febrile encephalitis, febrile illness, fever, formerly Human echovirus 22 23, gastroenteritis, gastrointestinal infections intracytoplasmic inclusion bodies, genital tract infections, haemolytic crisis in people with sickle cell disease, headaches, hemorrhagic fever, hemorrhagic fever w renal syndrome, herpetic encephalitis, Hodgkin's disease, Human coxsackievirus, Human coxsackievirus B1-6, Human echovirus 1-7 9 11-21 24-27 29-33, Human enterovirus 69, Human enterovirus 71 (hand foot and mouth disease), Human hepatitis virus A (HHAV), Human poliovirus, Human rhinovirus 1 2 7 9 11 15 16 21 29 36 39 49 50 58 62 65 85 89 hyperacute respiratory disease, Human rhinovirus 3 14 72, hyperacute respiratory disease, immune deficiency syndrome, infantile diarrhea, Infection with any dengue serotype (1-4), infectious mononucleosis, joint pain, Kaposi's sarcoma, keratoconjunctivitis, Kuru, lesions of coutanous sites, leucopoenia, liver cirrhosis, lower respiratory tract infection, lymphadenopathy, maculopapular rash, malignant tissue, measles, meningitis, mononucleosis (kissing disease), mumps, muscle pains, myocarditis, nephropathy, nephropathy in transplant patients, numbness, old world, opportunistic infection, oral infections, oral mucosa, orchitis, pancreatitis, pandemics, papilloma, paralysis, persistent infection of the kidney, persistent infections, persistent lymphopathy, pharyngeal conjunctivitis, pneumonia, primary hepatocellular carcinoma, pulmonary syndrome, rabies, rash, recurrent epidemics of respiratory disease, respiratory disease, respiratory illness, Roseola infantum, sarcoma, scarring, sever chills arthralgia, severe acute respiratory syndrome, severe encephalitis, shingles, sixth disease, skin and mucous membrane lesions, slim disease, sore throat, subacute sclerosing panencephalitis, superinfection with Deltavirus, ulceration, upper respiratory tract illness, Venezuelan hemorrhagic fever, vesicular pharyngitis, vesicular stomatitis with exanthema, viral polyarthritis and rush, viral warts, watery diarrhea, weakness, zoonotic, zoster, metaplasia, dysplasia, anaplasia, desmoplasia, carcinoma in situ, flu (influenza), invasive carcinoma, as well as any disease directly or indirectly related to the above mentioned viruses.

Examples of Viruses:

Information about the viruses can be found on Internet at the following link:

http://www.ncbi.nlm.nih.gov/ICTVdb/Ictv/ICD-10.htm

A non exhaustive list of viruses and their species which can be deactivated and therefore prevented from multiplication by the compositions of the present invention is as follows: Abadina virus (Reoviridae), Abelson murine leukemia virus (Retroviridae), Abras virus (Bunyaviridae), Absettarov virus (Flaviviridae), Abu Hammad virus (Bunyaviridae), Abu Mina virus (Bunyaviridae), Acado virus (Reoviridae), Acara virus (Bunyaviridae), Acciptrid herpesvirus (Herpesviridae), *Acheta domestica* densovirus (Parvoviridae), *Acrobasis zelleri* entomopoxvirus (Poxviridae), Adelaide River virus (Rhabdoviridae), Adeno-associated virus (Parvoviridae), *Aedes aegypti* densovirus (Parvoviridae), *Aedes aegypti* entomopoxvirus (Poxviridae), *Aedes albopictus* densovirus (Parvoviridae), *Aedes pseudoscutellaris* densovirus (Parvoviridae), African green monkey cytomegalovirus (Herpesviridae), African green monkey HHV-like virus (Herpesviridae), African green monkey polyomavirus (Papovaviridae), African horse sickness viruses (Reoviridae), African swine fever virus, African swine fever-like viruses, AG-virus (Bunyaviridae), AG-virus, (Bunyaviridae), *Agaricus bisporus* virus, Aguacate virus (Bunyaviridae), Ahlum water-borne virus (Tombusviridae), Aino virus (Bunyaviridae), Akabane virus (Bunyaviridae), AKR (endogenous) murine leukemia virus (Retroviridae), Alajuela virus (Bunyaviridae), Alcelaphine herpesvirus (Herpesviridae), Alenquer virus (Bunyaviridae), Aleutian disease virus (Parvoviridae), Aleutian mink disease virus (Parvoviridae), Alfuy virus (Flaviviridae), Allerton virus (Herpesviridae), Allitrich herpesvirus (Herpesviridae), *Allomyces arbuscula* virus, Almeirim virus (Reoviridae), Almpiwar virus (Rhabdoviridae), Altamira virus, (Reoviridae), Amapari virus (Arenaviridae), American ground squirrel herpesvirus, (Herpesviridae), *Amsacta moorei* entomopoxvirus (Poxviridae), Amyelosis chronic stunt virus (Caliciviridae), Ananindeua virus (Bunyaviridae), Anatid herpesvirus (Herpesviridae), Andasibe virus (Reoviridae), Anhanga virus (Bunyaviridae), Anhembi virus (Bunyaviridae), *Anomala cuprea* entomopoxvirus (Poxviridae), *Anopheles* A virus (Bunyaviridae), *Anopheles* virus (Bunyaviridae), Antequera virus (Bunyaviridae), Aotine herpesvirus (Herpesviridae), Apeu virus (Bunyaviridae), *Aphodius tasmaniae* entomopoxvirus (Poxviridae), Apoi virus (Flaviviridae), Aransas Bay virus (Bunyaviridae), Arbia virus (Bunyaviridae), Arboledas virus (Bunyaviridae), Arbroath virus (Reoviridae), Argentine turtle herpesvirus (Herpesviridae), Arkonam virus (Reoviridae), Aroa virus (Flaviviridae), *Arphia conspersa* entomopoxvirus (Poxviridae), Aruac virus (Rhabdoviridae), Arumowot virus (Bunyaviridae), Asinine herpesvirus (Herpesviridae), Atlantic cod ulcus syndrome virus (Rhabodoviridae), Atlantic salmon reovirus Australia (Reoviridae), Atlantic salmon reovirus Canada (Reoviridae), Atlantic salmon reovirus USA (Reoviridae), *Atropa belladorma* virus (Rhabdoviridae), *Aucuba bacilliform* virus, Badnavirus, Aujeszky's disease virus (Herpesviridae), Aura virus (Togaviridae), Auzduk disease virus (Poxviridae), Avalon virus (Bunyaviridae), Avian adeno-associated virus (Parvoviridae), Avian carcinoma, Mill Hill virus (Retroviridae), Avian encephalomyelitis virus (Picornaviridae), Avian infectious bronchitis virus (Coronaviridae), Avian leukosis virus—RSA (Retroviridae), Avian myeloblastosis virus (Retroviridae), Avian myelocytomatosis virus (Retroviridae), Avian nephrites virus (Picornaviridae), Avian paramyxovirus (Paramyxoviridae), Avian reovirus (Reoviridae), B virus (Parvoviridae), B-lymphotropic papovavirus (Papovaviridae), Babahoya virus (Bunyaviridae), Babanki virus (Togaviridae), Baboon herpesvirus (Herpesviridae), Baboon polyomavirus (Papovaviridae), Bagaza virus (Flaviviridae), Bahia Grande virus (Rhabdoviridae), Bahig virus (Bunyaviridae), Bakau virus (Bunyaviridae), Baku virus (Reoviridae), Bald eagle herpesvirus (Herpesviridae), Bandia virus (Bunyaviridae), Bangoran virus (Rhabdoviridae), Bangui virus (Bunyaviridae), Banzi virus (Flaviviridae), Barmah Forest virus (Togaviridae), Barranqueras virus (Bunyaviridae), Barur virus (Rhabdoviridae), Batai virus (Bunyaviridae), Batarna virus (Bunyaviridae), Batken virus (Bunyaviridae), Bauline virus (Reoviridae), Beak and feather disease virus (Circoviridae), BeAn virus (Rhabdoviridae), BeAr virus (Bunyaviridae), Bebaru virus (Togaviridae), Belem virus (Bunyaviridae), Belmont virus ((Bunyaviridae)), Belterra virus (Bunyaviridae), Benevides virus (Bunyaviridae), Benfica virus (Bunyaviridae), Berne virus, (Coronaviridae), Berrimah virus (Rhabdoviridae), Bertioga virus (Bunyaviridae), Bhanja virus (Bunyaviridae), Bimbo virus (Rhabdoviridae), Bimiti virus (Bunyaviridae), Birao virus (Bunyaviridae), BivensArm virus (Rhabdoviridae), BK virus (Papovaviridae), Bluetongue viruses (Reoviridae), Bobaya virus (Bunyaviridae), Bobia virus (Bunyaviridae), Bobwhite quail herpesvirus (Herpesviridae), Boid herpesvirus (Herpesviridae), *Bombyx mori* densovirus (Parvoviridae), Boolarra virus (Nodaviridae), Boraceia virus (Bunyaviridae), Border disease virus (Flaviviridae), Boma disease virus, Botambi virus (Bunyaviridae), Boteke virus, (Rhabdoviridae), Bouboui virus (Flaviviridae), Bovine adeno-associated virus (Parvoviridae), Bovine adenoviruses (Adenoviridae), Bovine astrovirus (Astroviridae), Bovine coronavirus (Coronaviridae), Bovine diarrhea virus (Flaviviridae), Bovine encephalitis herpesvirus (Herpesviridae), Bovine enteric calicivirus (Caliciviridae), Bovine enterovirus (Picornaviridae), Bovine ephemeral fever virus (Rhabdoviridae), Bovine herpesvirus (Herpesviridae), Bovine immunodeficiency virus (Retroviridae), Bovine leukemia virus (Retroviridae), Bovine mamillitis virus (Herpesviridae), Bovine papillomavirus (Papovaviridae), Bovine papular stomatitis virus (Poxviridae), Bovine parainfluenza virus (Paramyxoviridae), Bovine parvovirus (Parvoviridae), Bovine polyomavirus (Papovaviridae), Bovine respiratory syncytial virus (Paramyxoviridae), Bovine rhinovirus (Picornaviridae), Bovine syncytial virus (Retroviridae), Bozo virus (Bunyaviridae), Broadhaven virus (Reoviridae), Bruconha virus (Bunyaviridae), Brus Laguna virus (Bunyaviridae), Budgerigar fledgling disease virus (Papovaviridae), Buenaventura virus (Bunyaviridae), Buffalopox virus (Poxviridae), Buggy Creek virus (Togaviridae), Bujaru virus (Bunyaviridae), Bukalasa bat virus (Flaviviridae), Bunyamwera virus (Bunyaviridae), Bunyip creek virus (Reoviridae), Bushbush virus (Bunyaviridae), Bussuquara virus (Flaviviridae), Bwamba virus (Bunyaviridae), Cache Valley virus (Bunyaviridae), Cacipacore virus (Flaviviridae), Caddo Canyon virus (Bunyaviridae), Caimito virus (Bunyaviridae), Calchaqui virus (Rhabdoviridae), California encephalitis virus (Bunyaviridae), California harbor sealpox virus (Poxviridae), *Callistephus chinensis* chlorosis virus (Rhabdoviridae), Callitrichine herpesvirus (Herpesviridae), Camel contagious ecthyma virus (Poxviridae), Camelpox virus (Poxviridae), *Camptochironomus tentans* entomopoxvirus (Poxviridae), Cananeia virus (Bunyaviridae), Canarypox virus (Poxviridae), Candiru virus (Bunyaviridae), Canid herpesvirus (Herpesviridae), Caninde virus (Reoviridae), Canine adeno-associated virus (Parvoviridae), Canine adenovirus (Adenoviridae), Canine calicivirus (Caliciviridae), Canine coronavirus (Coronaviridae), Canine distemper virus (Paramyxoviridae), Canine herpesvirus (Herpesviridae), Canine minute virus (Parvoviridae), Canine oral papillomavirus (Papovaviridae), Canine parvovirus (Parvoviridae), *Canna* yellow mottle virus (Badnavirus), Cape Wrath virus (Reoviridae), Capim virus (Bunyaviridae), Caprine adenovirus (Adenoviridae), Caprine arthritis encephalitis virus (Retroviridae), Caprine herpesvirus (Herpesviridae), Capuchin herpesvirus AL- (Herpesviridae), Capuchin herpesvirus AP- (Herpesviridae), Carajas virus (Rhabdoviridae), Caraparu virus (Bunyaviridae), Carey Island virus (Flaviviridae), *Casphalia extranea* densovirus (Parvoviridae), Catu virus (Bunyaviridae), Caviid herpesvirus ((Herpesviridae)), CbaAr virus (Bunyaviridae), Cebine herpesvirus (Herpesviridae), Cercopithecine herpesvirus (Herpesviridae), Cervid herpesvirus (Herpesviridae), CG-virus (Bunyaviridae), Chaco virus (Rhabdoviridae), Chagres virus (Bunyaviridae), Chamois contagious ecthyma virus (Poxviridae), Chandipura virus (Rhabdoviridae), Changuinola virus (Reoviridae), Charleville virus (Rhabdoviridae), Chelonid herpesvirus (Herpesviridae), Chelonid herpesvirus (Herpesvirzdae), Chelonid herpesvirus (Herpesviridae), Chenuda virus (Reoviridae), Chick syncytial virus (Retroviridae), Chicken anemia virus (Circoviridae), Chicken parvovirus (Paruoviridae), Chikungunya virus (Togaviridae), Chilibre virus (Bunyaviridae), Chim virus (Bunyaviridae), Chimpanzee herpesvirus (Herpesviridae), *Chironomus attenuatus* entomopoxvirus (Poxviridae), *Chironomus luridus* entomopoxvirus (Poxviridae), *Chironomus plumosus* erltomopoxvirus (Poxviridae), Chobar Gorge virus (Reoviridae), *Choristoneura biennis* entomopoxvirus (Poxviridae), *Choristoneura conflicta* entomopoxvirus (Poxviridae), *Choristoneura diversuma* entomopoxvirus (Poxviridae), *Chorizagrotis auxiliars* entomopoxvirus (Poxviridae), Chub reovirus Germany (Reoviridae), Ciconiid herpesvirus (Herpesviridae), Clo Mor virus (Bunyaviridae), CoAr-virus (Bunyaviridae), Coastal Plains virus (Rhabdoviridae), Cocal virus (Rhabdoviridae), Coital exanthema virus (Herpesviridae), ColAn-virus (Bunyaviridae), Colocasia bobone disease virus, (Rhabdoviridae), Colorado tick fever virus, (Reoviridae), Columbia SK virus, (Picornaviridae), Columbid herpesvirus, (Herpesviridae), Connecticut virus, (Rhabdoviridae), Contagious ecthyma virus, (Poxviridae), Contagious pustular dermatitis virus, (Poxviridae), Corfu virus, (Bunyaviridae), Corriparta virus, (Reoviridae), Cotia virus, (Poxviridae), Cowpox virus, (Poxviridae), Crimean-Congo hemorrhagic fever virus, (Bunyaviridae), CSIRO village virus, (Reoviridae), Cynara virus, (Rhabdoviridae), Cyprinid herpesvirus, (Herpesviridae), Dabakala virus, (Bunyaviridae), D'Aguilar virus, (Reoviridae), Dakar bat virus, (Flaviviridae), DakArk virus, (Rhabdoviridae), Deer papillomavirus, (Papovaviridae), *Demodema boranensis* entomopoxvirus, (Poxviridae), Dengue virus, (Flaviviridae), Dengue virus group, (Flaviviridae), Dependovirus, (Parvoviridae), Dera Ghazi Khan virus, (Bunyaviridae), Dera Ghazi Khan virus Group, (Bunyaviridae), *Dermolepida albohirtum* entomopoxvirus, (Poxviridae), Dhori virus, (Orthomyxoviridae), *Diatraea saccharalis* densovirus, (Parvoviridae), Dobrava-Belgrade virus, (Bunyaviridae), Dolphin distemper virus, (Paramyxoviridae), Dolphinpox virus, (Poxviridae), Douglas virus, (Bunyaviridae), *Drosophila* C virus, (Picornaviridae), Dry Tortugas virus, (Bunyaviridae), duck adenovirus, (Adenoviridae), Duck adenovirus, (Adenoviridae), Duck astrovirus, (Astroviridae), Duck hepatitis B virus, (Hepadnaviridae), Duck plague herpesvirus syn. anatid herpesvirus, (Herpesviridae), Dugbe virus, (Bunyaviridae), Duvenhage virus, (Rhabdoviridae), Eastern equine encephalitis virus, (Togaviridae), Ebola virus Filoviridae, *Echinochloa hoja* blanca virus; Genus *Tenuivirus, Echinochloa* ragged stunt virus, (Reoviridae), ectromelia virus, (Poxviridae), Edge Hill virus, (Flaviviridae), Egtved virus syn. viral hemorrhagic septicemia virus, (Rhabdoviridae), Elapid herpesvirus, (Herpesviridae), Elephant loxondontal herpesvirus, (Herpesviridae), Elephant papillomavirus, (Papovaviridae), Elephantid herpesvirus, (Herpesviridae), Ellidaey virus, (Reoviridae), Embu virus, (Poxviridae), Encephalomyocarditis virus, (Picornaviridae), Enseada virus, (Bunyaviridae), Entamoeba virus, (Rhabdoviridae), Entebbe bat virus, (Flaviviridae), Epizootic hemorrhagic disease viruses, (Reoviridae), Epstein-Barr virus, (Herpesviridae), Equid herpesvirus, (Herpesviridae), Equid herpesvirus, (Nerpesviridae), Equid herpesvirus, (Herpesviridae), Equine abortion herpesvirus, (Herpesviridae), Equine adeno-associated virus, (Parvoviridae), Equine adenovirus, (Adenoviridae), Equine arteritis virus, (Arterivirus), Equine cytomegalovirus, (Herpesviridae), Equine encephalosis viruses, (Reoviridae), Equine herpesvirus, (Herpesviridae), Equine infectious anemia virus, (Retroviridae), Equine papillomavirus, (Papovaviridae), Equine rhinopneumonitis virus, (Herpesviridae), Equine rhinovirus, (Picornaviridae), Eret-virus, (Bunyaviridae), Erinaceid herpesvirus, (Herpesviridae), Erve virus, (Bunyaviridae), Erysimum latent virus, Tymovirus, Esocid herpesvirus, (Herpesviridae), Essaouira virus, (Reoviridae), Estero Real virus, (Bunyaviridae), Eubenangee virus, (Reoviridae), Euonymus fasciation virus, (Rhabdoviridae), European bat virus, (Rhabdoviridae), European brown hare syndrome virus, (Caliciviridae), European elk papillomavirus, (Papovaviridae), European ground squirrel cytomegalovirus, (Herpesviridae), European hedgehog herpesvirus, (Herpesviridae), Everglades virus, (Togaviridae), Eyach virus, (Reoviridae), Facey's Paddock virus, (Bunyaviridae), Falcon inclusion body disease, (Herpesviridae), Falconid herpesvirus, (Herpesviridae), Farallon virus, (Bunyaviridae), Felid herpesvirus, (Herpesviridae), Feline calicivirus, (Caliciviridae), Feline herpesvirus, (Herpesviridae), Feline immunodeficiency virus, (Retroviridae), Feline infectious peritonitis virus, (Coronaviridae), Feline leukemia virus, (Retroviridae), Feline parlleukopenia virus, (Parvoviridae), Feline parvovirus, (Parvoviridae), Feline syncytial virus, (Retroviridae), Feline viral rhinotracheitis virus, (Herpesviridae), Fetal rhesus kidney virus, (Papovaviridae), Field mouse herpesvirus, (Herpesviridae), Figulus subleavis entomopoxvirus, (Poxviridae), Fiji disease virus, (Reoviridae), Fin V-virus, (Bunyaviridae), Finkel-Biskis-Jinkins murine sarcoma virus, (Retroviridae), Flanders virus, (Rhabdoviridae), Flexal virus, (Arenaviridae), Flock house virus, Nodaviridae, Foot-and-mouth disease virus A, (Picornaviridae), Foot-and-mouth disease virus ASIA, (Picornaviridae), Foot-and-mouth disease virus, (Picornaviridae), Forecariah virus, (Bunyaviridae), Fort Morgan virus, (Togaviridae), Fort Sherman virus, (Bunyaviridae), Foula virus, (Reoviridae), Fowl adenoviruses, (Adenoviridae), Fowl calicivirus, (Caliciviridae), Fowlpox virus, (Poxviridae), Fraser Point virus, (Bunyaviridae), Friend murine leukemia virus, (Retroviridae), Frijoles virus, (Bunyaviridae), Frog herpesvirus, (Herpesviridae), Fromede virus, (Reoviridae), Fujinami sarcoma virus, (Retroviridae), Fukuoka virus, (Rhabdoviridae), Gabek Forest virus, (Bunyaviridae), Gadget's Gully virus, (Flaviviridae), *Galleria mellonella* densovirus, (Parvoviridae), Gallid herpesvirus, (Herpesviridae), Gamboa virus, (Bunyaviridae), Gan Gan virus, (Bunyaviridae), Garba virus, (Rhabdoviridae), Gardner-Arnstein feline sarcoma virus, (Retroviridae), *Geochelone carbonaria* herpesvirus, (Herpesviridae), *Geochelone chilensis* herpesvirus, (Herpesviridae), *Geotrupes sylvaticus* entomopoxvirus, (Poxviridae), Gerbera symptomless virus, (Rhabdoviridae), Germiston virus, (Bunyaviridae), Getah virus, (Togaviridae), Gibbon ape leukemia virus, (Retroviridae), Ginger chlorotic fleckvirus, Sobemovirus, Glycine mottle virus, Tombusviridae, Goat herpesvirus, (Herpesviridae), Goatpox virus, (Poxviridae), *Goeldichironomus holoprasimus* entomopoxvirus, (Poxviridae), Golden shiner reovirus, (Reoviridae), Gomoka virus, (Reoviridae), Gomphrena virus, (Rhabdoviridae), Gonometa virus, (Picornaviridae), Goose adenoviruses, (Adenoviridae), Goose parvovirus, (Parvoviridae), Gordil virus, (Bunyaviridae), Gorilla herpesvirus, (Herpesviridae), Gossas virus, (Rhabdoviridae), Grand Arbaud virus, (Bunyaviridae), Gray Lodge virus, (Rhabdoviridae), Gray patch disease agent of green sea turtle, (Herpesviridae), Great Island virus, (Reoviridae), Great Saltee Island virus, (Reoviridae), Great Saltee virus, (Bunyaviridae), Green iguana herpesvirus, (Herpesviridae), Green lizard herpesvirus, (Herpesviridae), Grey kangaroopox virus, (Poxviridae), Grimsey virus, (Reoviridae), Ground squirrel hepatitis B virus, (Hepadnaviridae), GroupA-K rotaviruses, (Reoviridae), Gruid herpesvirus, (Herpesviridae), GUU-virus, (Bunyaviridae), Guajara virus, (Bunyaviridae), Guama virus, (Bunyaviridae), Guanarito virus, (Arenaviridae), Guaratuba virus, (Bunyaviridae), Guaroa virus, (Bunyaviridae), Guinea pig cytomegalovirus, (Herpesviridae), Guinea pig herpesvirus, (Herpesviridae), Guinea pig type C oncovirus, (Retroviridae), Gumbo Limbo virus, (Bunyaviridae), Gurupi virus, (Reoviridae), H-virus, (Parvoviridae), H virus, (Bunyaviridae), Hamster herpesvirus, (Herpesviridae), Hamster polyomavirus, (Papovaviridae), Hantaan virus, (Bunyaviridae), Hanzalova virus, (Flaviviridae), Hardy-Zuckerman feline sarcoma virus, (Retroviridae), Hare fibroma virus, (Poxviridae), Hart Park virus, (Rhabdoviridae), Hartebeest herpesvirus, (Herpesviridae), Harvey murine sarcoma virus, (Retroviridae), Hazara virus, (Bunyaviridae), HB virus, (Parvoviridae), Hepatitis virus, (Picornaviridae), Hepatitis virus, (Hepadnaviridae), Hepatitis virus, (Flaviviridae), Herpesvirus M, (Herpesviridae), Herpesvirus papio, (Herpesviridae), Herpesvirus platyrrhinae type, (Herpesviridae), Herpesvirus pottos, (Herpesviridae), Herpesvirus saimiri, (Herpesviridae), Herpesvirus salmonis, (Herpesviridae), Herpesvirus sanguinus, (Herpesviridae), Herpesvirus scophthalmus, (Herpesviridae), Herpesvirus sylvilagus, (Herpesviridae), Herpesvirus T, (Herpesviridae), Herpesvirus tamarinus, (Herpesviridae), Highlands J virus, (Togaviridae), Hirame rhabdovirus, (Rhabdoviridae), Hog cholera virus, (Flaviviridae), HoJo virus, (Bunyaviridae), Hepatitis delta virus, Satellites, Deltavirus, Hsiung Kaplow herpesvirus, (Herpesviridae), Hepatitis E virus, (Caliciviridae), Hepatopancreatic parvo-like virus of shrimps, (Parvoviridae), Heron hepatitis B virus, (Hepadnaviridae), Herpes ateles, (Herpesviridae), Herpes simiae virus, (Herpesviridae), Herpes simplex virus, (Herpesviridae), Herpes virus B, (Herpesviridae), Herpesvirus aotus, (Herpesviridae), Herpesvirus ateles strain, (Herpesviridae), Herpesvirus cuniculi, (Herpesviridae), Herpesvirus cyclopsis, (Herpesviridae), Huacho virus, (Reoviridae), Hughes virus, (Bunyaviridae), Human adenoviruses, (Adenoviridae), Human astrovirus, (Astroviridae), Human calicivirus, (Caliciviridae), Human caliciviruses, (Caliciviridae), Human coronavirus E, (Coronaviridae), Human coronavirus OC, (Coronaviridae), Human coxsackievirus, (Picornaviridae), Human cytomegalovirus, (Herpesviridae), Human echovirus, (Picornaviridae), Human enterovirus, (Picornaviridae), Human foamy virus, (Retroviridae), Human herpesvirus, (Herpesviridae), Human herpesvirus, Nerpesviridae, Human herpesvirus, (Herpesviridae), Human immunodeficiency virus, (Retroviridae), Human papillomavirus, (Papovaviridae), Human parainfluenza virus, (Paramyxoviridae), Human poliovirus, (Picornaviridae), Human respiratory syncytial virus, (Paramyxoviridae), Human rhinovirus, (Picornaviridae), Human spumavirus, (Retroviridae), Human T-lymphotropic virus, (Retroviridae), Humpty Doo virus, (Rhabdoviridae), HV-virus, (Bunyaviridae), Hypr virus, (Flaviviridae), Laco virus, (Bunyaviridae), Ibaraki virus, (Reoviridae), Icoaraci virus, (Bunyaviridae), Ictalurid herpesvirus, (Herpesviridae), Len virus, (Reoviridae), Ife virus, (Reoviridae), Iguanid herpesvirus, (Herpesviridae), Ilesha virus, (Bunyaviridae), Ilheus virus, (Flaviviridae), Inclusion body rhinitis virus, (Herpesviridae), Infectious bovine rhinotracheitis virus, (Herpesviridae), Infectious bursal disease virus, Birnaviridae, Infectious hematopoietic necrosis virus, (Rhabdoviridae), Infectious laryngotracheitis virus, (Herpesviridae), Infectious pancreatic necrosis virus, Birnavirzdae, InfluenzaA virus (A/PR//(HN), (Orthomyxoviridae), Influenza B virus (B/Lee/), (Orthomyxoviridae), Influenza C virus (C/California/), (Orthomyxoviridae), Ingwavuma virus, (Bunyaviridae), Inini virus, (Bunyaviridae), Inkoo virus, (Bunyaviridae), Inner Frame virus, (Reoviridae), Ippy virus, (Arenaviridae), Irituia virus, (Reoviridae), Isfahan virus, (Rhabdoviridae), Israel turkey meningoencephalitis virus, (Flaviviridae), Issyk-Kul virus, (Bunyaviridae), Itaituba virus, (Bunyaviridae), Itaporanga virus, (Bunyaviridae), Itaqui virus, (Bunyaviridae), Itimirirn virus, (Bunyaviridae), Itupiranga virus, (Reoviridae), Jaagsiekte virus, (Retroviridae), Jacareacanga virus, (Reoviridae), Jamanxi virus, (Reoviridae), Jamestown Canyon virus, (Bunyaviridae), Japanaut virus, (Reoviridae), Japanese encephalitis virus, (Flaviviridae), Jan virus, (Reoviridae), JC virus, (Papovaviridae), Joa virus, (Bunyaviridae), Joinjakaka virus, (Rhabdoviridae), Juan Diaz virus, (Bunyaviridae), Jugra virus, (Flaviviridae), Juncopox virus, (Poxviridae), Junin virus, (Arenaviridae), *Junonia coenia* densovirus, (Parvoviridae), Jurona virus, (Rhabdoviridae), Jutiapa virus, (Flaviviridae), K virus, (Papovaviridae), K virus, (Bunyaviridae), Kachemak Bay virus, (Bunyaviridae), Kadarn virus, (Flaviviridae), Kaeng Khoi virus, (Bunyaviridae), Kaikalur virus, (Bunyaviridae), Kairi virus, (Bunyaviridae), Kaisodi virus, (Bunyaviridae), Kala Iris virus, (Reoviridae), Kamese virus, (Rhabdoviridae), Karnmavanpettai virus, (Reoviridae), Kannamangalam virus, (Rhabdoviridae), Kao Shuan virus, (Bunyaviridae), Karimabad virus, (Bunyaviridae), Karshi virus, (Flaviviridae), Kasba virus, (Reoviridae), Kasokero virus, (Bunyaviridae), Kedougou virus, (Flaviviridae), Kemerovo virus, (Reoviridae), Kenai virus, (Reoviridae), Kennedya virus Y, Potyviridae, Kern Canyon virus, (Rhabdoviridae), Ketapang virus, (Bunyaviridae), Keterah virus, (Bunyaviridae), Keuraliba virus, (Rhabdoviridae), Keystone virus, (Bunyaviridae), Kharagysh virus, (Reoviridae), Khasan virus, (Bunyaviridae), Kilham rat virus, (Parvoviridae), Kimberley virus, (Rhabdoviridae), Kindia virus, (Reoviridae), Kinkajou herpesvirus, (Herpesviridae), Kirsten murine sarcoma virus, (Retroviridae), Kismayo virus, (Bunyaviridae), Klamath virus, (Rhabdoviridae), Kokobera virus, (Flaviviridae), Kolongo virus, (Rhabdoviridae), Koolpinyah virus, (Rhabdoviridae), Koongol virus, (Bunyaviridae), Kotonkan virus, (Rhabdoviridae), Koutango virus, (Flaviviridae), Kowanyama virus, (Bunyaviridae), Kumlinge virus, (Flaviviridae), Kunjin virus, (Flaviviridae), Kwatta virus, (Rhabdoviridae), Kyzylagach virus, (Togaviridae), La Crosse virus, (Bunyaviridae), La Joya virus, (Rhabdoviridae), La-Piedad-Michoacan-Mexico virus, (Paramyxoviridae), Lacertid herpesvirus, (Herpesviridae), Lactate dehydrogenase-elevating virus, (Arterivirus), Lagos bat virus, (Rhabdoviridae), Lake Clarendon virus, (Reoviridae), Lake Victoria cormorant herpesvirus, (Herpesviridae), Langat virus, Flaviviridae, Langur virus, (Retroviridae), Lanjan virus, (Bunyaviridae), Lapine parvovirus, (Parvoviridae), Las Maloyas virus, (Bunyaviridae), Lassa virus, (Arenaviridae), Lato river virus, (Tombusviridae), Le Dantec virus, (Rhabdoviridae), Leanyer virus, (Bunyaviridae), Lebombo virus, (Reoviridae), Lednice virus, (Bunyaviridae), Lee virus, (Bunyaviridae), Leporid herpesvirus, (Herpesviridae), Leucorrhinia dubia densovirus, (Parvoviridae), Lipovnik virus, (Reoviridae), Liverpool vervet monkey virus, (Herpesviridae), Llano Seco virus, (Reoviridae), *Locusta migratona* entomopoxvirus, (Poxviridae), Lokem virus, (Bunyaviridae), Lone Star virus, (Bunyaviridae), Lorisine herpesvirus, (Herpesviridae), Louping ill virus, Flaviviridae, Lucke frog herpesvirus, (Herpesviridae), Lum virus, (Parvoviridae), Lukuni virus, (Bunyaviridae), Lumpy skin disease virus, (Poxviridae), Lundy virus, (Reoviridae), *Lymantria dubia* densovirus, (Parvoviridae), Lymphocytic choriomeningitis virus, (Arenaviridae), Machupo virus, (Arenaviridae), Macropodid herpesvirus (Herpesviridae), Madrid virus, (Bunyaviridae), Maguari virus, (Bunyaviridae), Main Drain virus, (Bunyaviridae), Malakal virus, (Rhabdoviridae), Malignant catarrhal fever virus of European cattle, (Herpesviridae), Malpais Spring virus, (Rhabdoviridae), *Malva silvestris* virus, (Rhabdoviridae), Manawa virus, (Bunyaviridae), Manawatu virus, (Nodaviridae), Manitoba virus, (Rhabdoviridae), Manzanilla virus, (Bunyaviridae), Map turtle herpesvirus, (Herpesviridae), Mapputta virus, (Bunyaviridae), Maprik virus, (Bunyaviridae), Maraba virus, (Rhabdoviridae), Marburg virus, (Filoviridae), Marco virus, (Rhabdoviridae), Marek's disease herpesvirus, (Herpesviridae), Marituba virus, (Bunyaviridae), Marmodid herpesvirus, (Herpesviridae), Marmoset cytomegalovirus, (Herpesviridae), Marmoset herpesvirus, (Herpesviridae), Marmosetpox virus, (Poxviridae), Marrakai virus, (Reoviridae), Mason-Pfizer monkey virus, (Retroviridae), Masou salmon reovirus, (Reoviridae), Matruh virus, (Bunyaviridae), Matucare virus, (Reoviridae), Mayaro virus, (Togaviridae), Mboke virus, (Bunyaviridae), Meaban virus, (Flaviviridae), Measles (Edmonston) virus, (Paramyxoviridae), Medical Lake macaque herpesvirus, (Herpesviridae), *Melanoplus sanguinipes* entomopoxvirus, (Poxviridae), Melao virus, (Bunyaviridae), Meleagrid herpesvirus, (Herpesviridae), Melilotus latent virus, (Rhabdoviridae), *Melolontha melolontha* entomopoxvirus, (Poxviridae), Mengovirus, (Picornaviridae), Mermet virus, (Bunyaviridae), Mice minute virus, (Parvoviridae), Mice pneumotropic virus, (Papovaviridae), *Microtus pennsylvanicus* herpesvirus, (Herpesviridae), Middelburg virus, (Togaviridae), Miller's nodule virus, (Poxviridae), Mill Door virus, (Reoviridae), Minatitlan virus, (Bunyaviridae), Mink calicivirus, (Caliciviridae), Mink enteritis virus, (Parvoviridae), Minnal virus, (Reoviridae), Mirabilis mosaic virus, Caulimovirus, Mirim virus, (Bunyaviridae), Mitchell river virus, (Reoviridae), Mobala virus, (Arenaviridae), Modoc virus, (Flaviviridae), Moju virus, (Bunyaviridae), Mojui dos Campos virus, (Bunyaviridae), Mokola virus, (Rhabdoviridae), *Molluscum contagiosum* virus, (Poxviridae), Molluscum-likepox virus, (Poxviridae), Moloney murine sarcoma virus, (Retroviridae), Moloney virus, (Retroviridae), Monkey pox virus, (Poxviridae), Mono Lake virus, (Reoviridae), Montana myotis leukoencephalitis virus, (Flaviviridae), Monte Dourado virus, (Reoviridae), Mopeia virus, (Arenaviridae), Moriche virus, (Bunyaviridae), Mosqueiro virus, (Rhabdoviridae), Mossuril virus, (Rhabdoviridae), Mount Elgon bat virus, (Rhabdoviridae), Mouse cytomegalovirus, (Herpesviridae), Mouse Elberfield virus, (Picornaviridae), Mouse herpesvirus strain, (Herpesviridae), Mouse mammary tumor virus, (Retroviridae), Mouse thymic herpesvirus, (Herpesviridae), Movar herpesvirus, (Herpesviridae), Mucambo virus, (Togaviridae), Mudjinbarry virus, (Reoviridae), Muir Springs virus, (Rhabdoviridae), Mule deerpox virus, (Poxviridae), Multimammate mouse papillomavirus, (Papovaviridae), Mumps virus, (Paramyxoviridae), Murid herpesvirus, (Herpesviridae), Murine adenovirus, (Adenoviridae), Z murine adenovirus, (Adenoviridae), Murine hepatitis virus, (Coronaviridae), Murine herpesvirus, (Herpesviridae), Murine leukemia virus, (Retroviridae), Murine parainfluenza virus, (Paramyxoviridae), Murine poliovirus, (Picornaviridae), Murine polyomavirus, (Papovaviridae), Murray Valley encephalitis virus, (Flaviviridae), Murre virus, (Bunyaviridae), Murutucu virus, (Bunyaviridae), Mykines virus, (Reoviridae), Mynahpox virus, (Poxviridae), Myxoma virus, (Poxviridae), Nairobi sheep disease virus, (Bunyaviridae), Naranjal virus, (Flaviviridae), Nasoule virus, (Rhabdoviridae), Navarro virus, (Rhabdoviridae), Ndelle virus, (Reoviridae), Ndumu virus, (Togaviridae), Neckar river virus, (Tombusviridae), Negishi virus, (Flaviviridae), Nelson Bay virus, New Minto virus, (Rhabdoviridae), Newcastle disease virus, (Paramyxoviridae), Ngaingan virus, (Rhabdoviridae), Ngari virus, (Bunyaviridae), Ngoupe virus, (Reoviridae), Nile crocodilepox virus, (Poxviridae), Nique virus, (Bunyaviridae), Nkolbisson virus, (Rhabdoviridae), Nola virus, (Bunyaviridae), North Clett virus, (Reoviridae), North End virus, (Reoviridae), Northern cereal mosaic virus, (Rhabdoviridae), Northern pike herpesvirus, (Herpesviridae), Northway virus, (Bunyaviridae), NorwaLk virus, (Caliciviridae), Ntaya virus, (Flaviviridae), Nugget virus, (Reoviridae), Nyabira virus, (Reoviridae), Nyamanini virus, Unassigned, Nyando virus, (Bunyaviridae), Oak-Vale virus, (Rhabdoviridae), Obodhiang virus, (Rhabdoviridae), Oceanside virus, (Bunyaviridae), Ockelbo virus, (Togaviridae), Odrenisrou virus, (Bunyaviridae), *Oedaleus senegalensis* entomopoxvirus, (Poxviridae), Oita virus, (Rhabdoviridae), Okhotskiy virus, (Reoviridae), Okola virus, (Bunyaviridae), Olifantsvlei virus, (Bunyaviridae), Omo virus, (Bunyaviridae), Omsk hemorrhagic fever virus, (Flaviviridae), *Onchorhynchus masou* herpesvirus, (Herpesviridae), O'nyong-nyong virus, (Togaviridae), *Operophtera brurnata* entomopoxvirus, (Poxviridae), Orangutan herpesvirus, (Herpesviridae), Orf virus, (Poxviridae), Oriboca virus, (Bunyaviridae), Oriximina virus, (Bunyaviridae), Oropouche virus, (Bunyaviridae), Orungo virus, (Reoviridae), Oryctes rhinoceros virus, Unassigned, Ossa virus, (Bunyaviridae), Ouango virus, (Rhabdoviridae), Oubi virus, (Bunyaviridae), Ourem virus, (Reoviridae), Ovine adeno-associated virus, (Parvoviridae), Ovine adenoviruses, (Adenoviridae), (Astroviridae), Ovine herpesvirus, (Herpesviridae), Ovine pulmonary adenocarcinoma virus, (Retroviridae), Owl hepatosplenitis herpesvirus, (Herpesviridae), P virus, (Bunyaviridae), Pacheco's disease virus, (Herpesviridae), Pacora virus, (Bunyaviridae), Pacui virus, (Bunyaviridae), Pahayokee virus, (Bunyaviridae), Palestina virus, (Bunyaviridae), Palyam virus, (Reoviridae), Pan herpesvirus, (Herpesviridae), Papio Epstein-Barr herpesvirus, (Herpesviridae), Para virus, (Bunyaviridae), Pararnushir virus, (Bunyaviridae), Parana virus, (Arenaviridae), Parapoxvirus of red deer in New Zealand, (Poxviridae), Paravaccinia virus, (Poxviridae), Parma wallaby herpesvirus, (Herpesviridae), Paroo river virus, (Reoviridae), Parrot herpesvirus, (Herpesviridae), Parry Creek virus, (Rhabdoviridae), Pata virus, (Reoviridae), Pates monkey herpesvirus pH delta, (Herpesviridae), Pathum Thani virus, (Bunyaviridae), Patois virus, (Bunyaviridae), Peaton virus, (Bunyaviridae), Percid herpesvirus, (Herpesviridae), Perdicid herpesvirus, (Herpesviridae), Perinet virus, (Rhabdoviridae), *Peripianata fuliginosa* densovirus, (Parvoviridae), Peste-des-petits-ruminants virus, (Paramyxoviridae), Petevo virus, (Reoviridae), Phalacrocoracid herpesvirus, (Herpesviridae), Pheasant adenovirus, (Adenoviridae), Phnom-Penh bat virus, (Flaviviridae), Phocid herpesvirus, (Herpesviridae), Phocine (seal) distemper virus, (Paramyxoviridae), Pichinde virus, (Arenaviridae), Picola virus, (Reoviridae), *Pieris rapae* densovirus, (Parvoviridae), Pigeon herpesvirus, (Herpesviridae), Pigeonpox virus, (Poxviridae), Badnavirus Piry virus, (Rhabdoviridae), *Pisum* virus, (Rhabdoviridae), Pixuna virus, (Togaviridae), Playas virus, (Bunyaviridae), Pleuronectid herpesvirus, (Nerpesviridae), Pneumonia virus of mice, (Paramyxoviridae), Pongine herpesvirus, (Herpesviridae), Pongola virus, (Bunyaviridae), Ponteves virus, (Bunyaviridae), Poovoot virus, (Reoviridae), Porcine adenoviruses, (Adenoviridae), Porcine astrovirus, (Astroviridae), Porcine circovirus, Circoviridae, Porcine enteric calicivirus, (Caliciviridae), Porcine enterovirus, (Picornaviridae), Porcine epidemic diarrhea virus, (Coronaviridae), Porcine hemagglutinating encephalomyelitis virus, (Coronaviridae), Porcine parvovirus, (Parvoviridae), Porcine respiratory and reproductive syndrome, (Arterivirus), Porcine rubulavirus, (Paramyxoviridae), Porcine transmissible gastroenteritis virus, (Coronaviridae), Porcine type C oncovirus, (Retroviridae), Porton virus, (Rhabdoviridae), Potosi virus, (Bunyaviridae), Powassan virus, (Flaviviridae), Precarious Point virus, (Bunyaviridae), Pretoria virus, (Bunyaviridae), Primate calicivirus, (Caliciviridae), Prospect Hill virus, (Bunyaviridae), *Pseudaletia includens* densovirus, (Parvoviridae), Pseudocowpox virus, (Poxviridae), Pseudolumpy skin disease virus, (Herpesviridae), Pseudorabies virus, (Herpesviridae), Psittacid herpesvirus, (Herpesviridae), Psittacinepox virus, (Poxviridae), Puchong virus, (Rhabdoviridae), Pueblo Viejo virus, (Bunyaviridae), Puffin Island virus, (Bunyaviridae), Punta Salinas virus, (Bunyaviridae), Punta Toro virus, (Bunyaviridae), Purus virus, (Reoviridae), Puumala virus, (Bunyaviridae), Qalyub virus, (Bunyaviridae), Quailpox virus, (Poxviridae), Quokkapox virus, (Poxviridae), Rabbit coronavirus, (Coronaviridae), Rabbit fibroma virus, (Poxviridae), Rabbit hemorrhagic disease virus, (Caliciviridae), Rabbit kidney vacuolating virus, (Papovaviridae), Rabbit oral papillomavirus, (Papovaviridae), Rabbitpox virus, (Poxviridae), Rabies virus, (Rhabdoviridae), Raccoon parvovirus, (Parvoviridae), Raccoonpox virus, (Poxviridae), Radi virus, (Rhabdoviridae), *Rangifer tarandus* herpesvirus, (Herpesviridae), Ranid herpesvirus, (Herpesviridae), *Raphanus* virus, (Rhabdoviridae), Rat coronavirus, (Coronaviridae), Rat cytomegalovirus, (Herpesviridae), Rat virus, R, (Parvoviridae), Raza virus, (Bunyaviridae), Razdan virus, (Bunyaviridae), Red deer herpesvirus, (Herpesviridae), Red kangaroopox virus, (Poxviridae), Reed Ranch virus, (Rhabdoviridae), herpesvirus, (Herpesviridae), Reindeer papillomavirus, (Papovaviridae), Reptile calicivirus, (Caliciviridae), Resistencia virus, (Bunyaviridae), Restan virus, (Bunyaviridae), Reticuloendotheliosis virus, (Retroviridae), Rhesus HHV-like virus, (Herpesviridae), Rhesus leukocyte associated herpesvirus strain, (Herpesviridae), Rhesus monkey cytomegalovirus, (Herpesviridae), Rhesus monkey papillomavirus, (Papovaviridae), Rheumatoid arthritis virus, (Parvoviridae), Rift Valley fever virus, (Bunyaviridae), Rinderpest virus, (Paramyxoviridae), Rio Bravo virus, (Flaviviridae), Rio Grande virus, (Bunyaviridae), RML virus, (Bunyaviridae), Rochambeau virus, (Rhabdoviridae), Rocio virus, (Flaviviridae), Ross River virus, (Togaviridae), Rost Islands virus, (Reoviridae), Rous sarcoma virus, (Retroviridae), Royal farm virus, (Flaviuiridae), RT parvovirus, (Parvoviridae), Rubella virus, (Togaviridae), Russian spring summer encephalitis virus, (Flaviviridae), S-virus, (Reoviridae), SA virus, (Herpesviridae), Sabio virus, (Arenaviridae), Sabo virus, (Bunyaviridae), Saboya virus, (Flaviviridae), Sacbrood virus, (Picornaviridae), Sagiyama virus, (Togaviridae), Saimiriine herpesvirus, (Herpesviridae), SaintAbb's Head virus, (Reoviridae), Saint-Floris virus, (Bunyaviridae), Sakhalin virus, (Bunyaviridae), Sal Vieja virus, (Flaviviridae), Salanga virus, (Bunyaviridae), Salangapox virus, (Poxviridae), Salehabad virus, (Bunyaviridae), Salmonid herpesvirus, (Herpesviridae), Salmonis virus, (Rhabdoviridae), *Sambucus* vein clearing virus, (Rhabdoviridae), SanAngelo virus, (Bunyaviridae), San Juan virus, (Bunyaviridae), San Miguel sealion virus, (Caliciviridae), San Perlita virus, (Flaviviridae), Sand rat nuclear inclusion agents, (Herpesviridae), Sandfly fever Naples virus, (Bunyaviridae), Sandfly fever Sicilian virus, (Bunyaviridae), Sandjimba virus, (Rhabdoviridae), Sango virus, (Bunyaviridae), Santa *Rosa* virus, (Bunyaviridae), Santarem virus, (Bunyaviridae), Sapphire II virus, (Bunyaviridae), Saraca virus, (Reoviridae), *Sarracenia purpurea* virus, (Rhabdoviridae), Sathuperi virus, (Bunyaviridae), Saumarez Reef virus, (Flaviviridae), Sawgrass virus, (Rhabdoviridae), *Schistocerca gregaria* entomopoxvirus, (Poxviridae), Sciurid herpesvirus, (Herpesviridae), Sciurid herpesvirus, (Herpesviridae), Sealpox virus, (Poxviridae), Seletar virus, (Reoviridae) Semliki Forest virus, (Togaviridae), Sena Madureira virus, (Rhabdoviridae), Sendai virus, (Paramyxoviridae), Seoul Virus, (Bunyaviridae), Sepik virus, (Flaviviridae), Serra do Navio virus, (Bunyaviridae), Shamonda virus, (Bunyaviridae), Shark River virus, (Bunyaviridae), Sheep associated malignant catarrhal fever of, (Herpesviridae), Sheep papillomavirus, (Papovaviridae), Sheep pulmonary adenomatosis associated herpesvirus, (Herpesviridae), Sheeppox virus, (Poxviridae), Shiant Islands virus, (Reoviridae), Shokwe virus, (Bunyaviridae), Shope fibroma virus, (Poxviridae), Shuni virus, (Bunyaviridae), Sibine fusca densovirus, (Parvoviridae), Sigma virus, (Rhabdoviridae), Sikte water-borne virus, (Tombusviridae), Silverwater virus, (Bunyaviridae), virus, (Bunyaviridae), Simian adenoviruses, (Adenoviridae), Simian agent virus, (Papovaviridae), Simian enterovirus, (Picornaviridae), Simian foamy virus, (Retroviridae), Simian hemorrhagic fever virus, (Arterivirus), Simian hepatitis A virus, (Picornaviridae), Simian immunodeficiency virus, (Retroviridae), Simian parainfluenza virus, (Paramyxoviridae), Simian rotavirus SA, (Reoviridae), Simian sarcoma virus, (Retroviridae), Simian T-lymphotropic virus, (Retroviridae), Simian type D virus, (Retroviridae), Simian vancella herpesvirus, (Herpesviridae), Simian virus, (Papovaviridae), *Simulium vittatum* densovirus, (Parvoviridae), Sindbis virus, (Togaviridae), Sixgun city virus, (Reoviridae), Skunkpox virus, (Poxviridae), Smelt reovirus, (Reoviridae), Snakehead rhabdovirus, (Rhabdoviridae), Snowshoe hare virus, (Bunyaviridae), Snyder-Theilen feline sarcoma virus, (Retroviridae), Sofyn virus, (Flaviviridae), Sokoluk virus, (Flaviviridae), Soldado virus, (Bunyaviridae), Somerville virus, (Reoviridae), Sparrowpox virus, (Poxviridae), Spectacled caimanpox virus, (Poxviridae), SPH virus, (Arenaviridae), Sphenicid herpesvirus, (Herpesviridae), Spider monkey herpesvirus, (Herpesviridae), Spondweni virus, (Flaviviridae), Spring viremia of carp virus, (Rhabdoviridae), Squirrel fibroma virus, (Poxviridae), Squirrel monkey herpesvirus, (Herpesviridae), Squirrel monkey retrovirus, (Retroviridae), SR-virus, (Bunyaviridae), Sripur virus, (Rhabdoviridae), StAbbs Head virus, (Bunyaviridae), St. Louis encephalitis virus, (Flaviviridae), Starlingpox virus, (Poxviridae), Stratford virus, (Flaviviridae), Strigid herpesvirus, (Herpesviridae), Striped bass reovirus, (Reoviridae), Striped Jack nervous necrosis virus, (Nodaviridae), Stump-tailed macaque virus, (Papovaviridae), Suid herpesvirus, (Herpesviridae), Sunday Canyon virus, (Bunyaviridae), Sweetwater Branch virus, (Rhabdoviridae), Swine cytomegalovirus, (Herpesviridae), Swine infertility and respiratory syndrome virus, (Arterivirus), Swinepox virus, (Poxviridae), Tacaiuma virus, (Bunyaviridae), Tacaribe virus, (Arenaviridae), Taggart virus, (Bunyaviridae), Tahyna virus, (Bunyaviridae), Tai virus, (Bunyaviridae), Taiassui virus, (Bunyaviridae), Tamana bat virus, (Flaviviridae), Tamdy virus, (Bunyaviridae), Tamiami virus, (Arenaviridae), Tanapox virus, (Poxviridae), Tanga virus, (Bunyaviridae), Tanjong Rabok virus, (Bunyaviridae), Taro bacilliform virus, (Badnavirus), Tataguine virus, (Bunyaviridae), Taterapox virus, (Poxviridae), Tehran virus, (Bunyaviridae), Telok Forest virus, (Bunyaviridae), Tembe virus, (Reoviridae), Tembusu virus, (Flaviviridae), Tench reovirus, (Reoviridae), Tensaw virus, (Bunyaviridae), Tephrosia symptomless virus, (Tombusviridae), Termeil virus, (Bunyaviridae), Tete virus, (Bunyaviridae), Thailand virus, (Bunyaviridae), Theiler's murine encephalomyelitis virus, (Picornaviridae), Thermoproteus virus, Lipothrixviridae, Thiafora virus, (Bunyaviridae), Thimiri virus, (Bunyaviridae), Thogoto virus, (Orthomyxoviridae), Thormodseyjarklettur virus, (Reoviridae), Thottapalayam virus, (Bunyaviridae), Tibrogargan virus, (Rhabdoviridae), Tickborne encephalitis virus, (Flaviviridae), Tillamook virus, (Bunyaviridae), Tilligerry virus, (Reoviridae), Timbo virus, (Rhabdoviridae), Tilmboteua virus, (Bunyaviridae), Tilmaroo virus, (Bunyaviridae), Tindholmur virus, (Reoviridae), Tlacotalpan virus, (Bunyaviridae), Toscana virus, (Bunyaviridae), Tradescantia/Zebrina virus, Potyviridae, Trager duck spleen necrosis virus, (Retroviridae), Tree shrew adenovirus, (Adenoviridae), Tree shrew herpesvims, (Herpesviridae), Triatoma virus, (Picornaviridae), Tribec virus, (Reoviridae), Trivittatus virus, (Bunyaviridae), Trombetas virus, (Bunyaviridae), Trubanarnan virus, (Bunyaviridae), Tsuruse virus, (Bunyaviridae), Tucunduba virus, (Bunyaviridae), Tumor virus X, (Parvoviridae), Tupaia virus, (Rhabdoviridae), Tupaiid herpesvirus, (Herpesviridae), Turbot herpesvirus, (Herpesviridae), Turbot reovirus, (Reoviridae), Turkey adenoviruses, (Adenoviridae), Turkey coronavirus, (Coronaviridae), Turkey herpesvirus, (Herpesviridae), Turkey rhinotracheitis virus, (Paramyxoviridae), Turkeypox virus, (Poxviridae), Turlock virus, (Bunyaviridae), Turuna virus, (Bunyaviridae), Tyuleniy virus, (Flaviviridae) Uasin Gishu disease virus, (Poxviridae), Uganda S virus, (Flaviviridae), Ulcerative disease rhabdovirus, (Rhabdoviridae), Umatilla virus, (Reoviridae), Umbre virus, (Bunyaviridae), Una virus, (Togaviridae), Upolu virus, (Bunyaviridae), UR sarcoma virus, (Retroviridae), Urucuri virus, (Bunyaviridae), Usutu virus, (Flaviviridae), Uting a virus, (Bunyaviridae), Utive virus, (Bunyaviridae), Uukuniemi virus, (Bunyaviridae) Vaccinia subspecies, (Poxviridae), Vaccinia virus, (Poxviridae), Vaeroy virus, (Reoviridae), Varicella-zoster virus, (Herpesviridae), Variola virus, (Poxviridae), Vellore virus, (Reoviridae), Venezuelan equine encephalitis virus, (Togaviridae), Vesicular exanthema of swine virus, (Caliciviridae), Vesicular stomatitis Alagoas virus, Rkabdoviridae, Vesicular stomatitis Indiana virus, (Rhabdoviridae), Vesicular stomatitis New Jersey virus, (Rhabdoviridae), Vilyuisk virus, (Picornaviridae), Vinces virus, (Bunyaviridae), Viper retrovirus, (Retroviridae), Viral hemorrhagic septicemia virus, (Rhabdoviridae), Virgin River virus, (Bunyaviridae), Virus III, (Herpesviridae), Visna/maedi virus, (Retroviridae), Volepoxvirus, (Poxviridae), Wad Medani virus, (Reoviridae), Wallal virus, (Reoviridae), Walleye epidermal hyperplasia, (Herpesviridae), Wanowrie virus, (Bunyaviridae), Warrego virus, (Reoviridae), Weddel water-borne virus, Tombusviridae, Weldona virus, (Bunyaviridae), Wesselsbron virus, (Flaviviridae), West Nile virus, (Flaviviridae), Western equine encephalitis virus, (Togaviridae), Wexford virus, (Reoviridae), Whataroa virus, (Togaviridae), Wildbeest herpesvirus, (Herpesviridae), Witwatersrand virus, (Bunyaviridae), Wongal virus, (Bunyaviridae), Wongorr virus, (Reoviridae), Woodchuck hepatitis B virus, (Hepadnaviridae), Woodchuck herpesvirus marmota, (Herpesviridae), Woolly monkey sarcoma virus, (Retroviridae), Wound tumor virus, (Reoviridae), WVU virus, (Reoviridae), WW virus, (Reoviridae), Wyeomyia virus, (Bunyaviridae), Xiburema virus, (Rhabdoviridae), Xingu virus, (Bunyaviridae), Y sarcoma virus, (Retroviridae), Yaba monkey tumor virus, (Poxviridae), Yaba-virus, (Bunyaviridae), Yaba-virus, (Bunyaviridae), Yacaaba virus, (Bunyaviridae), Yaounde virus, (Flaviviridae), Yaquina Head virus, (Reoviridae), Yata virus, (Rhabdoviridae), Yellow fever virus, (Flaviviridae), Yogue virus, (Bunyaviridae), Yokapox virus, (Poxviridae), Yokase virus, (Flaviviridae), Yucca baciliform virus, Badnavirus, Yug Bogdanovac virus, (Rhabdoviridae), Zaliv Terpeniya virus, (Bunyaviridae), *Zea mays* virus, (Rhabdoviridae), Zegla virus, (Bunyaviridae), Zika virus, (Flaviviridae), Zirqa virus, (Bunyaviridae).

Essential Oils:

Essential oils are volatile and liquid aroma compounds from natural sources, usually plants. Essential oils are not oils in a strict sense. Essential oils are usually prepared by fragrance extraction techniques such as distillation (including steam distillation), cold pressing, or extraction (maceration). Typically, essential oils are highly complex mixtures of often hundreds of individual chemical components.

A non limiting list of essential oils which can be used in the present invention is as follows (List D):

Agar oil, Ajwain oil, Angelica root oil, Anise oil (used medicinally), Asafoetida (used medicinally), Balsam oil, Basil oil, Bay (used in aromatheapeutic for sprains, colds, flu, insomnia, rheumatism), Bergamot oil (used in aromatherapy), Black Pepper essential oil (used for treating muscle aches, pains and strains), Buchu oil (used medicinally), Birch (aromatheapeutic used for gout, Rheumatism, Eczema, Ulcers), Camphor (used for cold, cough, fever, rheumatism, arthritis), *Cannabis* flower essential oil, Caraway oil (used in mouthwashes and toothpastes), Cardamom seed oil (used in aromatherapy and other medicinal applications), Carrot seed oil (used in aromatherapy), Cedarwood oil, Chamomile oil, Calamus Root (used medicinally), Cinnamon oil (used for flavoring and medicinally), Cistus species, Citronella oil (used medicinally), Clary Sage, Clove leaf oil (used as a topical anesthetic to relieve dental pain), Coriander, Costmary oil, Costus Root (used medicinally), Cranberry seed oil (equally high in omega-3 omega-6 fatty acids), Cubeb (used medicinally), Cumin oil/Black seed oil (used in veterinary medicine), Cypress, Cypriol, Curry leaf (used medicinally), Davana oil, Dill oil, Elecampane (used medicinally), Eucalyptus oil (used in medicine), Fennel seed oil (used medicinally, particularly for treating colic in infants), Fenugreek oil (used medicinally), Fir, Frankincense oil (used for aromatherapy), Galangal (used medicinally), Galbanum, Geranium oil (used medicinally), Ginger oil (used medicinally), Goldenrod, Grapefruit oil (used in aromatherapy), Henna oil (used medicinally), *Helichrysum*, Horseradish oil, Hyssop, Idaho Tansy, Jasmine oil, Juniper berry oil (used medicinally), Lavender oil (used medicinally), *Laurus nobilis*, Ledum, Lemon oil (used medicinally), Lemongrass (used to help treating fevers and infections), Lime (used as antiseptic, antiviral, bactericidal, disinfectant), *Litsea cubeba* oil, Mandarin, Marjoram, Melaleuca See Tea tree oil, Melissa oil (used medicinally), *Mentha arvensis* oil/Mint oil (used in flavoring toothpastes, mouthwashes and pharmaceuticals, as well as in aromatherapy and other medicinal applications), Mountain Savory, Mugwort oil, Mustard oil, Myrrh oil (used medicinally), Myrtle, Neem Tree Oil, Neroli (produced from the blossom of the bitter orange tree), Nutmeg, Orange oil, Oregano oil (contains thymol and carvacrol used to treat digestive problems), Orris oil (used medicinally), Palo Santo, Parsley oil, Patchouli oil, Perilla essential oil, Peppermint oil (used in a wide variety of medicinal applications), Petitgrain, Pine oil (used in aromatherapy), Ravensara, Red Cedar, Rose oil, Rosehip oil (used medicinally), Rosemary oil (used medicinally), Rosewood oil (used medicinally), Sage oil (used medicinally), Sandalwood oil, Sassafras oil (used medicinally), Savory oil, Schisandra oil (used medicinally), Spearmint oil, Spikenard (used medicinally), Spruce, Star anise oil (90% of the world's star anise crop is used in the manufacture of Tamiflu, a drug used to treat influenza, and is hoped to be useful for avian flu), Tangerine, Tarragon oil (used medicinally), Tea tree oil (used medicinally), Thyme oil (used medicinally), *Tsuga*, Turmeric (used medicinally), Valerian (used medicinally), Vetiver oil (khus oil), Western red cedar, Wintergreen, Yarrow oil (used medicinally), Ylang-ylang, Zedoary (used medicinally).

DETAILED DESCRIPTION OF THE INVENTION

Carvone forms two mirror image forms or enantiomers: R-(−)-carvone smells like spearmint. Its mirror image, S-(+)-carvone, smells like caraway. The fact that the two enantiomers are perceived as smelling differently is a proof that olfactory receptors must contain chiral groups, allowing them to respond more strongly to one enantiomer than to the other. Not all enantiomers have distinguishable odors. Squirrel monkeys have also been found to be able to discriminate between carvone enantiomers.

The two forms are also referred to by older names, with dextro-, d- referring to R-carvone, and laevo-, l- referring to S-carvone.

In chemistry, a racemic mixture, or racemate is one that has equal amounts of left- and right-handed enantiomers of a chiral molecule.

The present invention relates to S-(+)-carvone (also called (+)-carvone in the present invention) and R-(−)-carvone (also called (−)-carvone in the present invention).

Geraniol has two different diastereomers (also called cis-trans isomers) in the nature: Cis-geraniol and Trans-geraniol. The same applies for Cis-nerolidol and trans-nerolidol for example. In diastereomers the bond structure is the same, but the geometrical positioning of atoms and functional groups in space differs leading to different biological properties. For compounds with more than two substituents E-Z notation is used instead of trans and cis, respectively.

The present invention concerns Trans-geraniol.

The present invention relates to a composition comprising in combination R-(−)-2-methyl-5-(prop-1-en-2-yl)-cyclohex-2-enone (also called "(−) carvone") and S-(+)-2-methyl-5-(prop-1-en-2-yl)-cyclohex-2-enone (also called "(+) carvone") and (2E)-3,7-dimethylocta-2,6-dien-1-ol (also called trans-geraniol) and at least one more component chosen among essential oils components in a pharmaceutically effective concentration for use in treatment and prevention of diseases caused by DNA enveloped viruses, DNA non-enveloped viruses, RNA enveloped viruses and RNA non-enveloped viruses, said diseases are selected from the group consisting in:

(broncho)-pneumonia, 3 day fever exanthema, acute and chronic hepatitis, acute fever, acute gastroenteritis caused by strains such as Desert Shield Lordsdale Mexico Norwalk Hawaii Snow Mountain Southampton virus, acute gastroenteritis caused by strains such as Houston/86 Houston/90 London 29845 Manchester Parkville Sapporo virus, acute hepatitis, acute respiratory distress syndrome, AIDS, Argentine hemorrhagic fever, arthralgia, avian flu, Bolivian hemorrhagic fever, Brazilian hemorrhagic fever, chickenpox, chronic hepatitis, coma, common cold infection, common cold symptoms, congenital infection, conjunctivitis, contagious ecthyma, contagious pustular dermatitis, cornea, Creutzfeldt-Jakob-Disease, cryptic enteric infection, cytomegaloviral mononucleosis, dengue hemorrhagic fever (DHF), dengue shock syndrome (DSS), diarrhea, eczema, eczema herpaticum, encephalitis, encephalopathy, enteritis, epidemic nephropathy, epidemic polyarthritis and exanthema, epidermodysplasia veruciformis, Epstein-Barr virus infection, exanthema, exanthema in children, Fatal familial insomnia, febrile encephalitis, febrile illness, fever, formerly Human echovirus 22 23, gastroenteritis, gastrointestinal infections intracytoplasmic inclusion bodies, genital tract infections, haemolytic crisis in people with sickle cell disease, headaches, hemorrhagic fever, hemorrhagic fever w renal syndrome, herpetic encephalitis, Hodgkin's disease, Human coxsackievirus, Human coxsackievirus B1-6, Human echovirus 1-7 9 11-21 24-27 29-33, Human enterovirus 69, Human enterovirus 71 (hand foot and mouth disease), Human hepatitis virus A (HHAV), Human poliovirus, Human rhinovirus 1 2 7 9 11 15 16 21 29 36 39 49 50 58 62 65 85 89 hyperacute respiratory disease, Human rhinovirus 3 14 72, hyperacute respiratory disease, immune deficiency syndrome, infantile diarrhea, Infection with any dengue serotype (1-4), infectious mononucleosis, joint pain, Kaposi's sarcoma, keratoconjunctivitis, Kuru, lesions of coutanous sites, leucopoenia, liver cirrhosis, lower respiratory tract infection, lymphadenopathy, maculopapular rash, malignant tissue, measles, meningitis, mononucleosis (kissing disease), mumps, muscle pains, myocarditis, nephropathy, nephropathy in transplant patients, numbness, opportunistic infection, oral infections, orchitis, pancreatitis, pandemics, papilloma, paralysis, persistent infection of the kidney, persistent infections, persistent lymphopathy, pharyngeal conjunctivitis, pneumonia, primary hepatocellular carcinoma, pulmonary syndrome, rabies, rash, recurrent epidemics of respiratory disease, respiratory disease, respiratory illness, Roseola infantum, sarcoma, sever chills arthralgia, severe acute respiratory syndrome, severe encephalitis, shingles, sixth disease, skin and mucous membrane lesions, slim disease, sore throat, subacute sclerosing panencephalitis, superinfection with Deltavirus, ulceration, upper respiratory tract illness, Venezuelan hemorrhagic fever, vesicular pharyngitis, vesicular stomatitis with exanthema, viral polyarthritis and rush, viral warts, watery diarrhea, weakness, zoonotic, zoster, metaplasia, dysplasia, anaplasia, desmoplasia, carcinoma in situ, flu (influenza), invasive carcinoma.

The composition of the present invention is used for blocking the above mentioned viruses entering the host cell(s).

The composition of the present invention is also used as a prophylactic.

The composition of the present invention can be used as virus inhibitor within and outside the animal or human body.

The compositions of the present invention can also be used as a disinfectant.

The composition of the present invention can be administered, orally, topically, by inhalation, by suppository, intravenously, subcutaneously, or intramuscularly. It is also possible to spray a condom with the composition of the present invention said composition is intended to treat sexual transmitted diseases. The composition of the present invention can be manufactured in form of a solid (powder, tablets), or semi solid (creams, foams) or in form of a liquid or in form of a gas (aerosol).

Working Combinations:

The composition must comprise at least R-(−)-2-methyl-5-(prop-1-en-2-yl)-cyclohex-2-enone (this formula represents the component "(−) carvone") and S-(+)-2-methyl-5-(prop-1-en-2-yl)-cyclohex-2-enone (this formula represents the component "(+) carvone") and (2E)-3,7-dimethylocta-2,6-dien-1-ol (this formula represents the component "Trans geraniol").

The single general technical inventive concept of the present invention leading to a synergetic effect is:
the combination of R-(−)-2-methyl-5-(prop-1-en-2-yl)-cyclohex-2-enone and S-(+)-2-methyl-5-(prop-1-en-2-yl)-cyclohex-2-enone and (2E)-3,7-dimethylocta-2,6-dien-1-ol and at least one more component chosen among essential oils in a pharmaceutically effective concentration.

The chemical formula referring to "2-methyl-5-(prop-1-en-2-yl)-cyclohex-2-enone" is to be understood in the whole present invention as being the racemate of carvone, i.e. 50% of enantiomer R-(−)-2-methyl-5-(prop-1-en-2-yl)-cyclohex-2-enone and 50% of enantiomer S-(+)-2-methyl-5-(prop-1-en-2-yl)-cyclohex-2-enone.

The composition preferably comprises at least 10% by weight of each component. However, an amount of 10% to 35% by weight for each component may be preferable.

Using amounts less than 10% by weight of each component might conduct to a less effective antiviral effect.

Because the chemical structure of each component is very similar, thousands of working combinations are possible. Following are some of the tested working combinations (see the below mentioned examples) representing the most preferred embodiments of the present invention.

The common denominator for each composition of the below examples is R-(−)-2-methyl-5-(prop-1-en-2-yl)-cyclohex-2-enone and S-(+)-2-methyl-5-(prop-1-en-2-yl)-cyclohex-2-enone and (2E)-3,7-dimethylocta-2,6-dien-1-ol.

The composition of the present invention comprises R-(−)-2-methyl-5-(prop-1-en-2-yl)-cyclohex-2-enone and S-(+)-2-methyl-5-(prop-1-en-2-yl)-cyclohex-2-enone and (2E)-3,7-dimethylocta-2,6-dien-1-ol in combination with at least one more component selected from a list A consisting in:

LIST A: The 128 Essential Oils Components of the Present Invention are Defined as Follows:
  (−)-alpha-Pinene
  (−)-beta-Pinene
  (−)-Borneol
  (−)-Bornyl acetate
  (−)-Camphor
  (−)-Carveol
  (−)-Caryophyllene oxide
  (−)-Citronellal
  (−)-Citronellol
  (−)-Dihydrocarvyl acetate
  (−)-Fenchone
  (−)-Isopinocampheol
  (−)-Isopulegol
  (−)-Linalool
  (−)-Menthol
  (−)-Menthone
  (−)-Menthyl acetate
  (−)-Myrtenol
  (−)-Perillylalcohol
  (−)-trans-Myrtanol
  (−)-Verbenone
  (+)-2-Carene
  (+)-alpha-Pinene
  (+)-Borneol
  (+)-Camphor
  (+)-Citronellol
  (+)-Cuparene
  (+)-Dihydrocarveol (+)-Dihydrocarvone
(+)-Fenchone
(+)-Isomenthol
(+)-Isopinocampheol
(+)-Menthol
(+)-Neomenthol
(+/−)-alpha-Pinene
(+/−)-alpha-Pinene
(+/−)-beta-Citronellol
(+/−)-Camphor
(+/−)-Linalool
(+/−)-Menthol
(+/−)-Neomenthol
(1R)-Chrysanthemolactone
(1S,2S)-10-Pinanol
(cis+trans)-Nerolidol
1,4-Cineole
1,8-Cineole
2-Isopropyl-5-methylphenol
2-Norbornanone
3-Carene
3-Octanone
4-Menthan-3-one
Acetic acid butylester
Acetic acid cinnamylester
Acetic acid heptylester
Acetic acid isobutylester
Acetic acid methylester
alpha-(−)-Bisabolol
alpha-Caryophyllene
alpha-Cedrene
alpha-Humulene
alpha-Ionone
alpha-Terpinene
alpha-Terpineol
Azulene
Benzoic acid eugenylester
beta-Cedrene
beta-Naphthol
beta-Thujaplicin
Butyl acetate
Cajeputol
Camphene
Cedar camphor
Cedrol
Chamazulen
Cinnamyl acetate
cis-Jasmone
cis-Nerolidol
Citral
Citronellol
Cuminaldehyde
Cypress camphor
Dihydrocarveol
Dillapiole
DL-Citronellyl acetate
Estragole
Eucalyptol
Eugenol methylether
Eugenylbenzoate
exo-2-Camphanol
Farnesol
Furfuryl acetate
Furfuryl alcohol
gamma-Terpinene
Geranyl acetate
Heptyl acetate
Isobornyl acetate
Isobornyl isovalerate
Isobutyl acetate
Isocineole
Isoeugenol
Isoeugenylacetate
Isolongifolene
Isomenthone
Isothymol
Lemonol
Linalool
Linalool oxide
Linalyl acetate
Nerol
Nootkatone
p-Allylanisole
Piperitone
R-(−)-alpha-Phellandrene
R-(÷)-Limonene
R-(+)-Pulegone
S-(−)-Limonene
Sabinene
Sabinyl acetate
Terpinolene
Terpinyl acetate
Tetrahydrolinalool
trans-Nerolidol
trans-Stilbene
(cis+Trans)-1,2(+)-limonene oxide
Eugenol
farnesol
Lavendulol
Linalooloxide
in a pharmaceutically effective concentration for use in treatment and prevention of diseases caused by DNA enveloped viruses, DNA non-enveloped viruses, RNA enveloped viruses and RNA non-enveloped viruses,
said diseases are selected from the group consisting in:
(broncho)-pneumonia, 3 day fever exanthema, acute and chronic hepatitis, acute fever, acute gastroenteritis caused by strains such as Desert Shield Lordsdale Mexico Norwalk Hawaii Snow Mountain Southampton virus, acute gastroenteritis caused by strains such as Houston/86 Houston/90 London 29845 Manchester Parkville Sapporo virus, acute hepatitis, acute respiratory distress syndrome, AIDS, Argentine hemorrhagic fever, arthralgia, avian flu, Bolivian hemorrhagic fever, Brazilian hemorrhagic fever, chickenpox, chronic hepatitis, coma, common cold infection, common cold symptoms, congenital infection, conjunctivitis, contagious ecthyma, contagious pustular dermatitis, cornea, Creutzfeldt-Jakob-Disease, cryptic enteric infection, cytomegaloviral mononucleosis, dengue hemorrhagic fever (DHF), dengue shock syndrome (DSS), diarrhea, eczema, eczema herpaticum, encephalitis, encephalopathy, enteritis, epidemic nephropathy, epidemic polyarthritis and exanthema, epidermodysplasia veruciformis, Epstein-Barr virus infection, exanthema, exanthema in children, Fatal familial insomnia, febrile encephalitis, febrile illness, fever, formerly Human echovirus 22 23, gastroenteritis, gastrointestinal infections intracytoplasmic inclusion bodies, genital tract infections, haemolytic crisis in people with sickle cell disease, headaches, hemorrhagic fever, hemorrhagic fever w renal syndrome, herpetic encephalitis, Hodgkin's disease, Human coxsackievirus, Human coxsackievirus B1-6, Human echovirus 1-7 9 11-21 24-27

29-33, Human enterovirus 69, Human enterovirus 71 (hand foot and mouth disease), Human hepatitis virus A (HHAV), Human poliovirus, Human rhinovirus 1 2 7 9 11 15 16 21 29 36 39 49 50 58 62 65 85 89 hyperacute respiratory disease, Human rhinovirus 3 14 72, hyperacute respiratory disease, immune deficiency syndrome, infantile diarrhea, Infection with any dengue serotype (1-4), infectious mononucleosis, joint pain, Kaposi's sarcoma, keratoconjunctivitis, Kuru, lesions of coutanous sites, leucopoenia, liver cirrhosis, lower respiratory tract infection, lymphadenopathy, maculopapular rash, malignant tissue, measles, meningitis, mononucleosis (kissing disease), mumps, muscle pains, myocarditis, nephropathy, nephropathy in transplant patients, numbness, opportunistic infection, oral infections, orchitis, pancreatitis, pandemics, papilloma, paralysis, persistent infection of the kidney, persistent infections, persistent lymphopathy, pharyngeal conjunctivitis, pneumonia, primary hepatocellular carcinoma, pulmonary syndrome, rabies, rash, recurrent epidemics of respiratory disease, respiratory disease, respiratory illness, Roseola infantum, sarcoma, sever chills arthralgia, severe acute respiratory syndrome, severe encephalitis, shingles, sixth disease, skin and mucous membrane lesions, slim disease, sore throat, subacute sclerosing panencephalitis, superinfection with Deltavirus, ulceration, upper respiratory tract illness, Venezuelan hemorrhagic fever, vesicular pharyngitis, vesicular stomatitis with exanthema, viral polyarthritis and rush, viral warts, watery diarrhea, weakness, zoonotic, zoster, metaplasia, dysplasia, anaplasia, desmoplasia, carcinoma in situ, flu (influenza), invasive carcinoma.

The chemical components listed in the previously mentioned list A are components which are all present in different essential oils. The first component of list A is "(−)-alpha-Pinene" and the 128th and last component of list A is "Linalooloxide".

The following examples correspond to pharmaceutical compositions having an effective antiviral effect.

The compositions of the present invention may preferably contain 4, 5, 6, 7, 8, 9, 10 components or even more components (e.g. 11, 19, 35, 67 or 131 components or even more components). The word "component(s)" can also be replaced by the word "substance(s)" or "compound(s)".

The compositions of the present invention are defined as being the following compositions:

TABLE C

| Compositions of the present invention: | |
|---|---|
| EXAMPLE 1 | |
| Eugenol methylether | 1,2-dimethoxy-4-prop-2-enylbenzene |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |
| EXAMPLE 2 | |
| Cistral | 3,7-Dimethyl-2,6-octadienal |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |
| EXAMPLE 3 | |
| Eugenol methylether | 1,2-dimethoxy-4-prop-2-enylbenzene |
| Azulene | bicyclo[5.3.0]decapentaene |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |
| EXAMPLE 4 | |
| Eugenol methylether | 1,2-dimethoxy-4-prop-2-enylbenzene |
| Linalooloxide | 2-(5-ethenyl-5-methyloxolan-2-yl)propan-2-ol |
| (+)-Carvone | S-(+)-2-methyl-5-(prop-1-en-2-yl)-cyclohex-2-enone |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |
| EXAMPLE 5 | |
| Eugenol methylether | 1,2-dimethoxy-4-prop-2-enylbenzene |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| (−)-Borneol | 1,7,7-Trimethyl-bicyclo[2.2.1]heptan-2-ol |
| (−)-Carvone | R-(−)-2-methyl-5-(prop-1-en-2-yl)-cyclohex-2-enone |

TABLE C-continued

| Compositions of the present invention: | |
|---|---|
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 6

| | |
|---|---|
| Eugenol methylether | 1,2-dimethoxy-4-prop-2-enylbenzene |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-Borneol | 1,7,7-Trimethyl-bicyclo[2.2.1]heptan-2-ol |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 7

| | |
|---|---|
| Eugenol methylether | 1,2-dimethoxy-4-prop-2-enylbenzene |
| Linalooloxide | 2-(5-ethenyl-5-methyloxolan-2-yl)propan-2-ol, |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Cistral | 3,7-Dimethyl-2,6-octadienal |
| (+)-Carvone | S-(+)-2-methyl-5-(prop-1-en-2-yl)-cyclohex-2-enone |

EXAMPLE 8

| | |
|---|---|
| Farnesol | (2E,6E)-3,7,11-trimethyldodeca-2,6,10-trien-1-ol |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 9

| | |
|---|---|
| Eugenol methylether | 1,2-dimethoxy-4-prop-2-enylbenzene |
| Eucalyptol | 4,7,7-trimethyl-8-oxabicyclo[2.2.2]octane |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 10

| | |
|---|---|
| Eugenol methylether | 1,2-dimethoxy-4-prop-2-enylbenzene |
| Linalooloxide | 2-(5-ethenyl-5-methyloxolan-2-yl)propan-2-ol |
| Geraniol | (2E)-3,7-dimethylocta-2,6-dien-1-ol |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 11

| | |
|---|---|
| Eugenol methylether | 1,2-dimethoxy-4-prop-2-enylbenzene |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| (−)-Menthol | 5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 12

| | |
|---|---|
| Eugenol methylether | 1,2-dimethoxy-4-prop-2-enylbenzene |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| 2-Methyl-l-butanol | 2-methylbutan-1-ol |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 13

| | |
|---|---|
| Eugenol methylether | 1,2-dimethoxy-4-prop-2-enylbenzene |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |

TABLE C-continued

Compositions of the present invention:

| | |
|---|---|
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| 4-Cymene | 1-methyl-4-propan-2-ylbenzene |
| (+)-Carvone | S-(+)-2-methyl-5-(prop-1-en-2-yl)-cyclohex-2-enone |

EXAMPLE 14

| | |
|---|---|
| Farnesyl acetate | 3,7,11-trimethyldodeca-2,6,10-trienyl acetate |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 15

| | |
|---|---|
| Eugenol methylether | 1,2-dimethoxy-4-prop-2-enylbenzene |
| (−)-Menthylacetate | [(1R,2S,5R)-5-methyl-2-propan-2-ylcyclohexyl] acetate |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 16

| | |
|---|---|
| Eugenol methylether | 1,2-dimethoxy-4-prop-2-enylbenzene |
| Linalooloxide | 2-(5-ethenyl-5-methyloxolan-2-yl)propan-2-ol |
| Isomenthone | 5-methyl-2-propan-2-ylcyclohexan-1-one |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 17

| | |
|---|---|
| Eugenol methylether | 1,2-dimethoxy-4-prop-2-enylbenzene |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| trans-Nerolidol | (6E)-3,7,11-trimethyldodeca-1,6,10-trien-3-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 18

| | |
|---|---|
| Eugenol methylether | 1,2-dimethoxy-4-prop-2-enylbenzene |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| R-(+)-Limonene | (4R)-1-methyl-4-prop-1-en-2-ylcyclohexene |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 19

| | |
|---|---|
| Eugenol methylether | 1,2-dimethoxy-4-prop-2-enylbenzene |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| (+)-Carvone | S-(+)-2-methyl-5-(prop-1-en-2-yl)-cyclohex-2-enone |

EXAMPLE 20

| | |
|---|---|
| Guaiazulene | 1,4-dimethyl-7-propan-2-ylazulene |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | |

EXAMPLE 21

| | |
|---|---|
| Eugenol methylether | 1,2-dimethoxy-4-prop-2-enylbenzene |
| 2-Methyl-l-butanol | 2-methylbutan-1-ol |

TABLE C-continued

Compositions of the present invention:

| | |
|---|---|
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 22

| | |
|---|---|
| Eugenol methylether | 1,2-dimethoxy-4-prop-2-enylbenzene |
| Linalooloxide | 2-(5-ethenyl-5-methyloxolan-2-yl)propan-2-ol |
| (−)-Menthylacetate | [(1R,2S,5R)-5-methyl-2-propan-2-ylcyclohexyl] acetate |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 23

| | |
|---|---|
| Eugenol methylether | 1,2-dimethoxy-4-prop-2-enylbenzene |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| 1,4-cisneole | 4-methyl-1-propan-2-yl-7-oxabicyclo[2.2.1]heptane |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 24

| | |
|---|---|
| Eugenol methylether | 1,2-dimethoxy-4-prop-2-enylbenzene |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (+)-DihydrocalVeol | 2-methyl-2-prop-1-en-2-ylcyclohexan-1-ol |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 25

| | |
|---|---|
| Eugenol methylether | 1,2-dimethoxy-4-prop-2-enylbenzene |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| (−)-Isopulegol | 5-methyl-2-prop-1-en-2-ylcyclohexan-1-ol |
| (+)-Carvone | S-(+)-2-methyl-5-(prop-1-en-2-yl)-cyclohex-2-enone |

EXAMPLE 26

| | |
|---|---|
| alpha-Ionone | (E)-4-(2,6,6-trimethylcyclohex-2-en-1-yl)but-3-en-2-one |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 27

| | |
|---|---|
| Eugenol methylether | 1,2-dimethoxy-4-prop-2-enylbenzene |
| R-(+)-Pulegone | 5-methyl-2-propan-2-ylidenecyclohexan-1-one |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 28

| | |
|---|---|
| Eugenol methylether | 1,2-dimethoxy-4-prop-2-enylbenzene |
| Linalooloxide | 2-(5-ethenyl-5-methyloxolan-2-yl)propan-2-ol |
| (cis+trans)-Nerolidol | 3,7,11-trimethyldodeca-1,6,10-trien-3-ol |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

TABLE C-continued

Compositions of the present invention:

EXAMPLE 29

| | |
|---|---|
| Eugenol methylether | 1,2-dimethoxy-4-prop-2-enylbenzene |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| 4-(4-Methoxyphenyl)-2-butanone | 4-(4-methoxyphenyl)butan-2-one |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 30

| | |
|---|---|
| Eugenol methylether | 1,2-dimethoxy-4-prop-2-enylbenzene |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| 2-Methyl-3-buten-2-ol | 2-methylbut-3-en-2-ol |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 31

| | |
|---|---|
| Eugenol methylether | 1,2-dimethoxy-4-prop-2-enylbenzene |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| cis-Jasmone | 3-methyl-2-[(Z)-pent-2-enyl]cyclopent-2-en-1-one |
| (+)-Carvone | S-(+)-2-methyl-5-(prop-1-en-2-yl)-cyclohex-2-enone |

EXAMPLE 32

| | |
|---|---|
| cis-Jasmone | 3-methyl-2-[(Z)-pent-2-enyl]cyclopent-2-en-1-one |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 33

| | |
|---|---|
| Eugenol methylether | 1,2-dimethoxy-4-prop-2-enylbenzene |
| alpha-Terpinene | 1-methyl-4-propan-2-ylcyclohexa-1,3-diene |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 34

| | |
|---|---|
| Eugenol methylether | 1,2-dimethoxy-4-prop-2-enylbenzene |
| Linalooloxide | 2-(5-ethenyl-5-methyloxolan-2-yl)propan-2-ol |
| (−)-cistronellol | (3S)-3,7-dimethyloct-6-en-1-ol |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 35

| | |
|---|---|
| Eugenol methylether | 1,2-dimethoxy-4-prop-2-enylbenzene |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| Cinnamyl lacetate | [(E)-3-phenylprop-2-enyl] acetate |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 36

| | |
|---|---|
| Eugenol methylether | 1,2-dimethoxy-4-prop-2-enylbenzene, |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |

TABLE C-continued

Compositions of the present invention:

| | |
|---|---|
| (+1−)-Linalool | 3,7-dimethylocta-1,6-dien-3-ol |
| (+)-Carvone | S-(+)-2-methyl-5-(prop-1-en-2-yl)-cyclohex-2-enone |

EXAMPLE 37

| | |
|---|---|
| alpha-(−)-Bisabolol | (2R)-6-methyl-2-[(1R)-4-methyl-1-cyclohex-3-enyl]hept-5-en-2-ol |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 38

| | |
|---|---|
| Eugenol methylether | 1,2-dimethoxy-4-prop-2-enylbenzene |
| (−)-Isopinocampheol | 2,7,7-trimethylbicyclo[3.1.1]heptan-3-ol |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 39

| | |
|---|---|
| Eugenol methylether | 1,2-dimethoxy-4-prop-2-enylbenzene |
| Linalooloxide | 2-(5-ethenyl-5-methyloxolan-2-yl)propan-2-ol |
| Eucalyptol | 4,7,7-trimethyl-8-oxabicyclo[2.2.2]octane |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 40

| | |
|---|---|
| Isoeugenol | 2-methoxy-4-[(E)-prop-1-enyl]phenol |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 41

| | |
|---|---|
| Eugenol methylether | 1,2-dimethoxy-4-prop-2-enylbenzene |
| gamma-Nonalactone | 5-pentyloxolan-2-one |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 42

| | |
|---|---|
| Eugenol methylether | 1,2-dimethoxy-4-prop-2-enylbenzene |
| Linalooloxide | 2-(5-ethenyl-5-methyloxolan-2-yl)propan-2-ol |
| (+)-Neomenthol | (1S,2S,5R)-5-methyl-2-propan-2-ylcyclohexan-1-ol |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 43

| | |
|---|---|
| Eugenol methylether | 1,2-dimethoxy-4-prop-2-enylbenzene |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| Cuminaldehyde | 4-propan-2-ylbenzaldehyde |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 44

| | |
|---|---|
| Eugenol methylether | 1,2-dimethoxy-4-prop-2-enylbenzene |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |

TABLE C-continued

Compositions of the present invention:

| | |
|---|---|
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| R-(+)-Limonene | (4R)-1-methyl-4-prop-1-en-2-ylcyclohexene |
| (+)-Carvone | S-(+)-2-methyl-5-(prop-1-en-2-yl)-cyclohex-2-enone |

EXAMPLE 45

| | |
|---|---|
| Isoeugenylacetate | [2-methoxy-4-[(E)-prop-1-enyl]phenyl] acetate |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 46

| | |
|---|---|
| Eugenol methylether | 1,2-dimethoxy-4-prop-2-enylbenzene |
| Menthyl salicylate | (5-methyl-2-propan-2-ylcyclohexyl) 2-hydroxybenzoate |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 47

| | |
|---|---|
| Eugenol methylether | 1,2-dimethoxy-4-prop-2-enylbenzene |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| (+)-Borneol | 1,7,7-trimethylbicyclo[2.2.1]heptan-6-ol |
| (+)-Carvone | S-(+)-2-methyl-5-(prop-1-en-2-yl)-cyclohex-2-enone |

EXAMPLE 48

| | |
|---|---|
| Eugenol methylether | 1,2-dimethoxy-4-prop-2-enylbenzene |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-cistronellol | (3S)-3,7-dimethyloct-6-en-1-ol |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 49

| | |
|---|---|
| (cis+trans)-1,2-(−)-Limonene oxide | 1-methyl-4-prop-1-en-2-yl-7-oxabicyclo[4.1.0]heptane |
| Linalooloxide | 2-(5-ethenyl-5-methyloxolan-2-yl)propan-2-ol |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 50

| | |
|---|---|
| Eugenol methylether | 1,2-dimethoxy-4-prop-2-enylbenzene |
| DL-cistronellyl acetate | 3,7-dimethyloct-6-enyl acetate |
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 51

| | |
|---|---|
| Eugenol methylether | 1,2-dimethoxy-4-prop-2-enylbenzene |
| Linalooloxide | 2-(5-ethenyl-5-methyloxolan-2-yl)propan-2-ol |
| Eugenol | 2-methoxy-4-prop-2-enylphenol |
| (+/−)-Isomenthol | (1R,2S,5S)-5-methyl-2-propan-2-ylcyclohexan-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 52

| | |
|---|---|
| Eugenol methylether | 1,2-dimethoxy-4-prop-2-enylbenzene |
| Linalooloxide | 2-(5-ethenyl-5-methyloxolan-2-yl)propan-2-ol |

TABLE C-continued

Compositions of the present invention:

| | |
|---|---|
| (cis+trans)-1,2-(+)-Limonene oxide | 1-methyl-4-prop-1-en-2-yl-7-oxabicyclo[4.1.0]heptane |
| (+/−)-Isomenthol | (1R,2S,5S)-5-methyl-2-propan-2-ylcyclohexan-1-ol |
| gamma-Nonalactone | 5-pentyloxolan-2-one |
| Trans-Geraniol | (2E)-3,7-dimethylocta-2,6-dien-1-ol |
| Eugenol | 2-methoxy-4-prop-2-enylphenol |
| (+)-Carvone | S-(+)-2-methyl-5-(prop-1-en-2-yl)-cyclohex-2-enone |

EXAMPLE 53

| | |
|---|---|
| trans-Nerolidol | (6E)-3,7,11-trimethyldodeca-1,6,10-trien-3-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2,7,7-trimethylbicyclo[3.1.1]heptan-3-ol |
| (+)-Carvone | S-(+)-2-methyl-5-(prop-1-en-2-yl)-cyclohex-2-enone |

EXAMPLE 54

| | |
|---|---|
| (cis+trans)-Nerolidol | 3,7,11-trimethyldodeca-1,6,10-trien-3-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2,7,7-trimethylbicyclo[3.1.1]heptan-3-ol |
| (+)-Carvone | S-(+)-2-methyl-5-(prop-1-en-2-yl)-cyclohex-2-enone |

EXAMPLE 55

| | |
|---|---|
| Lavendulol | (±)-2-Isopropenyl-5-methyl-4-hexen-1-ol |
| (−)-Carvone | R-(−)-2-methyl-5-(prop-1-en-2-yl)-cyclohex-2-enone |
| Trans-Geraniol | (2E)-3,7-dimethylocta-2,6-dien-1-ol |
| Eugenol | 2,7,7-trimethylbicyclo[3.1.1]heptan-3-ol |
| (+)-Carvone | S-(+)-2-methyl-5-(prop-1-en-2-yl)-cyclohex-2-enone |

EXAMPLE 56

(−)-Carvone
(+)-Carvone
Trans-Geraniol
combined with the 128 components listed in list A

EXAMPLE 57

(−)-Carvone
(+)-Carvone
Trans-Geraniol
combined with the 64 first components listed in list A

EXAMPLE 58

(−)-Carvone
(+)-Carvone
Trans-Geraniol
combined with the 64 last components listed in list A (i.e. the 65th to the 128th components)

EXAMPLE 59

(−)-Carvone
(+)-Carvone
Trans-Geraniol
combined with the 32 first components listed in list A

EXAMPLE 60

(−)-Carvone
(+)-Carvone
Trans-Geraniol
combined with the 32 last components listed in list A (i.e. the 97th to the 128th components)

EXAMPLE 61

(−)-Carvone
(+)-Carvone
Trans-Geraniol
combined with the 16 first components listed in list A

EXAMPLE 62

(−)-Carvone
(+)-Carvone
Trans-Geraniol
combined with the 16 last components listed in list A (i.e. the 113th to the 128th components)

EXAMPLE 63

(−)-Carvone
(+)-Carvone
Trans-Geraniol
combined with the 8 first components listed in list A TABLE C-continued Compositions of the present invention:

EXAMPLE 64

(−)-Carvone
(+)-Carvone
Trans-Geraniol
combined with the 8 last components listed in list A (i.e. the 121th to the 128th components)

EXAMPLE 65

(−)-Carvone
(+)-Carvone
Trans-Geraniol
combined with the 4 first components listed in list A

EXAMPLE 66

(−)-Carvone
(+)-Carvone
Trans-Geraniol
combined with the 4 last components listed in list A (i.e. the 125th to the 128th components)

EXAMPLE 67

(−)-Carvone
(+)-Carvone
Trans-Geraniol
combined with the 2 first components listed in list A

EXAMPLE 68

(−)-Carvone
(+)-Carvone
Trans-Geraniol
combined with the 2 last components listed in list A (i.e. the 127th to the 128th components)

EXAMPLE 69

(−)-Carvone
(+)-Carvone
Trans-Geraniol
combined with the first component listed in list A: (−)-alpha-Pinene

EXAMPLE 70

(−)-Carvone
(+)-Carvone
Trans-Geraniol
combined with the 128th component listed in list A: Linalooloxide Each component of the above mentioned examples can have a weight percentage (wt %) comprised between 0.05 and 80, or preferably between 5 to 50 or between 10 to 50 or between 10 to 35, more preferably between 0.05 and 35, most preferably between 5 and 35.

Each component contained in a composition of the above mentioned examples may contain the same or different ranges (in wt %) chosen among the previously mentioned ranges (in wt %). One or more component(s) contained in a composition of the above mentioned examples may also have different ranges (in wt %) as those previously mentioned.

Any specific component of any above mentioned example of Table C can be combined with any other specific component of any other example mentioned above in Table C in order to form a new composition.

3,7-Dimethyl-1,6-octadien-3-yl acetate can be replaced by other catalysers (components) depending on the type of application.

Certain components of the composition of the present invention can be enantiomer positive and/or enantiomer negative. Certain components do not have enantiomers. Other components can have Cis-isomer and/or Trans-isomer.

In the unprobable case that one or more of the above mentioned example(s) would have been known from a prior art document, we reserve the right to disclaim such example from the present invention.

The composition of the present invention may comprise at least 2-methyl-5-(prop-1-en-2-yl)-cyclohex-2-enone and (2E)-3,7-dimethylocta-2,6-dien-1-ol in combination with at least one more component in a pharmaceutically effective concentration for use in treatment and prevention of diseases caused by DNA enveloped viruses, DNA non-enveloped viruses, RNA enveloped viruses, RNA non-enveloped viruses said diseases are selected from the group consisting in:

(broncho)-pneumonia, 3 day fever exanthema, acute and chronic hepatitis, acute fever, acute gastroenteritis caused by strains such as Desert Shield Lordsdale Mexico Norwalk Hawaii Snow Mountain Southampton virus, acute gastroenteritis caused by strains such as Houston/86 Houston/90 London 29845 Manchester Parkville Sapporo virus, acute hepatitis, acute respiratory distress syndrome, AIDS, Argentine hemorrhagic fever, arthralgia, avian flu, Bolivian hemorrhagic fever, Brazilian hemorrhagic fever, chickenpox, chronic hepatitis, coma, common cold infection, common cold symptoms, congenital infection, conjunctivitis, contagious ecthyma, contagious pustular dermatitis, cornea, Creutzfeldt-Jakob-Disease, cryptic enteric infection, cytomegaloviral mononucleosis, dengue hemorrhagic fever (DHF), dengue shock syndrome (DSS), diarrhea, eczema, eczema herpaticum, encephalitis, encephalopathy, enteritis, epidemic nephropathy, epidemic polyarthritis and exanthema, epidermodysplasia veruciformis, Epstein-Barr virus infection, exanthema, exanthema in children, Fatal familial insomnia, febrile encephalitis, febrile illness, fever, formerly Human echovirus 22 23, gastroenteritis, gastrointestinal infections intracytoplasmic inclusion bodies, genital tract infections, haemolytic crisis in people with sickle cell disease, headaches, hemorrhagic fever, hemorrhagic fever w renal syndrome, herpetic encephalitis, Hodgkin's disease, Human coxsackievirus, Human coxsackievirus B1-6, Human echovirus 1-7 9 11-21 24-27 29-33, Human enterovirus 69, Human enterovirus 71 (hand foot and mouth disease), Human hepatitis virus A (HHAV), Human poliovirus, Human rhinovirus 1 2 7 9 11 15 16 21 29 36 39 49 50 58 62 65 85 89 hyperacute respiratory disease, Human rhinovirus 3 14 72, hyperacute respiratory disease, immune deficiency syndrome, infantile diarrhea, Infection with any dengue serotype (1-4), infectious mononucleosis, joint pain, Kaposi's sarcoma, keratoconjunctivitis, Kuru, lesions of coutanous sites, leucopoenia, liver cirrhosis, lower respiratory tract infection, lymphadenopathy, maculopapular rash, malignant tissue, measles, meningitis, mononucleosis (kissing disease), mumps, muscle pains, myocarditis, nephropathy, nephropathy in transplant patients, numbness, opportunistic infection, oral infections, orchitis, pancreatitis, pandemics, papilloma, paralysis, persistent infection of the kidney, persistent infections, persistent lymphopathy, pharyngeal conjunctivitis, pneumonia, primary hepatocellular carcinoma, pulmonary syndrome, rabies, rash, recurrent epidemics of respiratory disease, respiratory disease, respiratory illness, Roseola infantum, sarcoma, sever chills arthralgia, severe acute respiratory syndrome, severe encephalitis, shingles, sixth disease, skin and mucous membrane lesions, slim disease, sore throat, subacute sclerosing panencephalitis, superinfection with Deltavirus, ulceration, upper respiratory tract illness, Venezuelan hemorrhagic fever, vesicular pharyngitis, vesicular stomatitis with exanthema, viral polyarthritis and rush, viral warts, watery diarrhea, weakness, zoonotic, zoster, metaplasia, dysplasia, anaplasia, desmoplasia, carcinoma in situ, flu (influenza), invasive carcinoma.

The present invention can also consist in a composition comprising a compound having a chemical Structure of formula A and Anti-viral properties in Vivo. This compound can be used as a medicament.

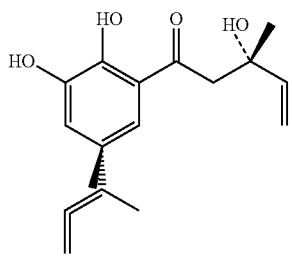

$C_{16}H_{22}O_4$  Formula A

In order to produce this compound the man skilled in the art has two options.

Option 1:
Synthesize the compound using above-mentioned blueprint from scratch according to standard known synthesizing procedures used in the medical, food flavoring and fragrance industry. E.g. International Foods and Fragrances (USA), Givaudan (Swiss).

Option 2:
Combine existing components available in industry and attain an as close as possible combination, using the above mentioned compound (formula A) as a blueprint.

The man skilled in the art has over 40,000 natural registered Monoterpenes and over 60,000 Sequeterpenes to his disposal and obviously there are thousands possible combinations leading to the required chemical structure presented above.

An alternative similar compound having a chemical structure of formula B can also lead to production of an Antiviral medicament.

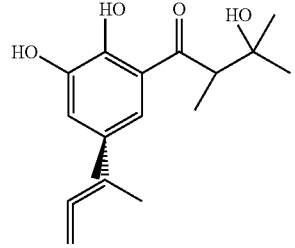

$C_{16}H_{22}O_4$  Formula B

Minor deviations to the above blue print are possible to have a lesser or similar anti-viral effect in Vivo.

In order to prove the efficacy of above-mentioned compounds, the inventor has combined certain more common components (see Components list of Table C).

First, it was confirmed that none of the single components taken alone of the list had any anti viral effect In Vivo.

Further, components were identified that were common in all the tested formulations:
Carvone(+), Carvone(−) and Trans-Geraniol.

As the majority of the components have very similar chemical structures, it is no undue burden for a man skilled in the art having both the blue print (formula A and B) of the ideal anti viral and 100,000 registered components to his disposal to combine several alternative components to achieve a similar result.

The composition of the present invention comprises a pharmaceutical compound of formula A or B:

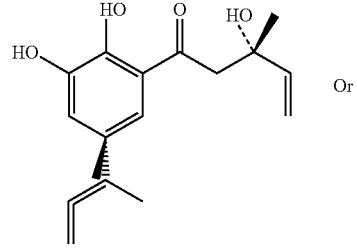

Formula A

Or

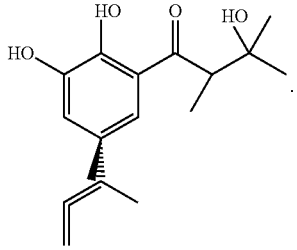

Formula B

An example of a composition of the present invention comprises the following component(s) in the following ranges (wt %):

TABLE 1

| Components of a preferred embodiment of the composition (example 53) | Range 1 in wt. % | More preferred Range 2 in wt. % | Most preferred Range 3 in wt. % |
|---|---|---|---|
| trans-Nerolidol | 0.05 to 80 | 10 to 50 | 10 to 35 |
| (−)-Carvone | 0.05 to 80 | 10 to 50 | 10 to 35 |
| Trans-Geraniol | 0.05 to 80 | 10 to 50 | 10 to 35 |
| Eugenol | 0.05 to 80 | 10 to 50 | 10 to 35 |
| (+)-Carvone | 0.05 to 80 | 10 to 50 | 10 to 35 |

All values (i.e. any limit value of a range) mentioned on a same line in the above table can be combined together in order to form a new range combination for the specific component comprised in the composition.

The aim of table 1 is to give examples of ranges and specific values found for a specific component by techniques well known by a person skilled in the art.

Advantage of the Present Invention

An advantage of the antiviral compositions according to the present invention consists in that the composition is a mixture of components and so no simultaneous resistance can be developed to them all by the viruses. Moreover, the non-specific activity of the composition according to the invention is different to that of conventional drugs, enabling them to effectively treat and prevent diseases and not to be affected by the possible emergence of virus mutation.

Another advantage of the compositions according to the invention is that the components are lipophilic, being therefore able to easily cross between body and cellular compartments and accumulate in lipid-rich tissues.

Being volatile, the components of the compositions according to the invention can be excreted via the lungs: an added advantage when treating and preventing respiratory infections or inflammations. The components of the composition can be diffused into the atmosphere and fall onto exposed surface, deactivating viruses before they reach a potential host.

In order to prove the efficacy of the composition of the present invention, in vivo studies have been conducted. Following are examples of at least one virus belonging to each of the 4 major viral families.

In Vivo Tests:

Individual case studies were performed by medical practitioners that confirmed the potent activity of the present invention against all existing 4 families of viruses, namely:

DNA enveloped viruses (e.g. Herpes virus, *Molluscum contagiosum*, Varicella-zoster).

DNA non-enveloped viruses (e.g. Papillomavirus, Parvovirus, Adenovirus).

RNA enveloped viruses (e.g. Hepatitis C, Porcine reproductive and respiratory syndrome virus (PPRS virus), Coronavirus).

RNA non-enveloped viruses (e.g. Rotavirus, Rhinovirus, Coxsackievirus).

Studies conducted by veterinarians involving over 700 animals, several observational studies on humans and ongoing double-blinded placebo controlled phase III clinical trials confirmed the efficiency of the present invention and did not show any toxic side effect.

In the present invention the novel synergetic antiviral compositions of Table C are always instilled on or in animals or humans after the viruses infected the animal or human body.

Mode of Action

The composition of the present invention deactivates viruses when they are in the free state, i.e. when they are not associated with cells, by interfering with the surface tension of the lipid coating of the viruses capsules thereby preventing the entry of the viruses in the animal or human cells and therefore the multiplication of the viruses in the cells. This had been determined by in vitro technology. This is in direct contrast to existing antiviral products, which only exert an effect once the viruses are associated with host cells. The composition of the present invention can act as an anti-infectious agent, inactivating viral particles before they contact the host. There is only one common mode of action of the composition of the present invention involved in all diseases; therefore there should be no need to provide tests for all diseases or all viruses specifically mentioned in the present application.

In Vivo Results:

The following examples have been taken from cases study results to highlight the activity of the antiviral composition for which the specific composition of example 1 and example 53 (see Table C) have been used in order to conduct all the mentioned tests. In the present invention the novel synergetic composition is always instilled on or in animals or humans after the viruses infected the animal or human body in order to treat animal or human diseases. The man skilled in the art knows how to perform the tests.

| Component(s) | Percentage by weight |
|---|---|
| Composition of Example 53 contains (see Table C): | |
| R-(−)-2-methyl-5-(prop-1-en-2-yl)-cyclohex-2-enone (−)-Carvone | 12.5% |
| S-(+)-2-methyl-5-(prop-1-en-2-yl)-cyclohex-2-enone (+)-Carvone | 12.5% |
| (2E)-3,7-dimethylocta-2,6-dien-1-ol Trans-Geraniol | 25% |
| 2-methoxy-4-prop-2-enylphenol Eugenol | 25% |
| (6E)-3,7,11-trimethyldodeca-1,6,10-trien-3-ol Trans-Nerolidol | 25% |
| Composition of Example 1 contains (see Table C): | |
| Eugenol methylether | 12.5% |
| Linalooloxide | 12.5% |
| (cis+trans)-1,2-(+)-Limonene oxide | 12.5% |
| (+/−)-Isomenthol | 12.5% |
| (−)-Carvone | 12.5% |
| Trans-Geraniol | 12.5% |
| Eugenol | 12.5% |
| (+)-Carvone | 12.5% |

Similar or identical results showing an antiviral effect would have been achieved by using any combination of components defined in claim 1 of the present invention and/or in examples 1 to 70 of the present invention (see Table C).

RNA Enveloped Virus—Hepatitis C Virus:

In most instances, there is a slow, progressive asymptomatic hepatitis with persistent viraemia lasting many years. Only 5% of those infected show symptoms. Chronic infection occurs in 80% of those infected, showing a variety of debilitating conditions including kidney disease and 20% develop cirrhosis and hepatocellular carcinoma. Infection is caused by direct contact with contaminated blood and mother to infant transfer in commonplace.

The drug of choice is with IFN-alpha, but many cases relapse when the drug is stopped and less than 15% are permanently cured after more than a year of treatment.

Similar or identical results as with the composition of example 1 or example 53 (see Table C) would have been achieved by using any combination of components defined in claim 1 of the present invention and/or in examples 1 to 70 of the present invention (see Table C).

Methods:

Patients:

Adult patients who had not previously taken interferon and who had the following characteristics were eligible for the study: a positive test for anti-HCV antibody, an HCV RNA level greater than 2000 copies per milliliter on polymerase-chain-reaction analysis, a serum alanine amino-transferase concentration above the upper limit of normal on two occasions during the preceding six months, and findings consistent with a diagnosis of chronic hepatitis C on liver biopsy performed during the preceding year, as determined by a single, study-designated pathologist.

Assessment and Endpoints:

Because of the specific mode of action of the composition, which is genotype neutral, no Hepatitis C virus genotyping was performed. The primary efficacy end points were an early virologic response (significant lowering of HCV RNA on analysis).

Results:

Characteristics of the Patients:

Of the 11 patients enrolled, 6 met the criteria for entry. Base loads ranged from 22,000,000 to 11,600. Five (5) patients were enrolled for a one-time 1 to 4 week treatment. One patient was enrolled for a long-term treatment.

Efficacy: 1-4 Weeks

All 6 patients were administered 350 µg of the composition of the present invention three times daily.

TABLE 2

Virological and Biological Response at Week 4
according to Intention-to-Treat Analysis

| P | Name | Date | Base | LO | Date | Base + 1 | Log | EVR | Log |
|---|------|------|------|-----|------|----------|-----|-----|-----|
| 1 | Sherif | 5/01/2007 | 22.000.000 | 7.3 | 17/01/2007 | 1.360.000 | 6.1 | 94% | 1.2 |
| 3 | Adel | 26/01/2007 | 290.000 | 5.5 | 10/02/2007 | 54.020 | 4.7 | 81% | 0.7 |
| 7 | Fawzy | 17/02/2007 | 1.118.572 | 6.0 | 11/03/2007 | 111.144 | 5.0 | 90% | 1.0 |
| 8 | Fathy | 18/02/2007 | 1.950.00 | 6.3 | 13/03/2007 | 165.055 | 5.2 | 92% | 1.1 |
| 11 | Magded | 17/01/2007 | 11.600 | 4.1 | 04/03/2007 | 1.864 | 3.3 | 84% | 0.8 |
| 2 | Fatma | 17/01/2007 | 825.000 | 5.9 | 27/01/2007 | 501.000 | 5.7 | 39% | 0.2 |

Efficacy of treatment with the composition was associated with a significant drop in viral load comparable with traditional treatment with peginterferon alfa-2a.

Similar or identical results as with the composition of example 1 or example 53 (see Table C) would have been achieved by using any combination of components defined in claim 1 of the present invention and/or in examples 1 to 70 of the present invention (see Table C).

Efficacy: Interrupted Trial:

One patient was treated over a period of 30 weeks, during which the treatment was interrupted and restarted three times within three different intervals. He was administered the same dose, 350 µg of the composition three times daily for intervals ranging from 1 to 4 weeks.

Similar or identical results as with the composition of example 1 or example 53 (see Table C) would have been achieved by using any combination of components defined in claim 1 of the present invention and/or in examples 1 to 70 of the present invention (see Table C).

Conclusion:

Multiple interruptions of the treatment with the composition did not affect its positive virological response, confirming its mode of action.

DNA Non-enveloped Virus—Papilloma Virus:

A papilloma is a benign epithelial growth commonly referred to as a wart or verruca and is caused by over 40 different strains of Human Papillomavirus (HPV). The appearance and seriousness of the infection varies from one anatomical region to another. Genital warts is now considered to be the most common sexually transmitted disease in the USA, with over 6 million new cases a year and with over 30 million carriers in the USA alone. There is a strong association with HPV infection and cancer of the reproductive tract.

Test Results

The efficacy of the composition of the present invention on the Papilloma virus was performed on a stressed businessman, aged 34, who regularly endured outbreaks of genital viral warts due to the papilloma virus. This tended to occur once every two weeks. The composition was administered orally under the medical supervision of a doctor, 300 mg thrice daily for three days at the onset of an outbreak and the symptoms subsided. After 3 weeks all warts had disappeared. The patient reported no side effects and remains asymptomatic after 18 months.

Similar or identical results as with the composition of example 1 or example 53 (see Table C) would have been achieved by using any combination of components defined in claim 1 of the present invention and/or in examples 1 to 70 of the present invention (see Table C).

Ongoing Randomized Placebo-Controlled Clinical Trial

A ongoing randomized, double-blind, placebo controlled trial at an Mexican Hospital is being conducted to compare

TABLE 3

Virological and Biological Response with variable interruptions
Intention-to-Treat Analysis

| | Test | Date | Viral Load | LOG | WKs | LOG | Start/Stop |
|---|------|------|------------|-----|-----|-----|------------|
| 1 | Base | 05/01/2007 | 22.000.000 | 7.3 | | | |
| 2 | PCR 01 | 17/01/2007 | 1.360.000 | 6.1 | 2 | −1.2 | |
| 3 | PCR 02 | 24/01/2007 | 453.000 | 5.7 | 1 | −0.5 | Interruption of treatment |
| 4 | PCR 03 | 01/02/2007 | 5.658.000 | 6.8 | 1 | 1.1 | Restart of treatment |
| 5 | PCR 04 | 17/02/2007 | 1.118.572 | 6.0 | 2 | −0.7 | |
| 6 | PCR 05 | 12/03/2007 | 165.055 | 5.2 | 3 | −0.8 | Interruption of treatment |
| 7 | PCR 06 | 01/07/2007 | 4.498.635 | 6.7 | 10 | 1.4 | Restart of treatment |
| 8 | PCR 07 | 28/08/2007 | 1.150.008 | 6.1 | 4 | −0.6 | | the effectiveness and the patient tolerance of the composition of the present invention topically applied spray with those of a placebo spray in the treatment of viral induced cervical lesions. The results of this initial part of the study will also help to determine changes the treatment protocols, changes in recruitment, enrollment, and follow-up for the rest of the study. All subjects had cervical lesions, as confirmed by colposcopy examination. In the initial group 28 subjects were screened; 24 were confirmed positive. Sixteen were eliminated; four had cervical atrophy and 12 were excluded from the efficacy analysis for protocol violations. There were 10 subjects in the intent-to-treat analysis, and a separate efficacy analysis was done on four subjects. In total each subject was treated eight times in a period of four days. There was no difference between the two groups at baseline with respect to any clinical or demographic factor. Neither group experienced adverse effects. More than 65% of the lesions in the group treated with the composition of the present invention started to disappear after 1 day and nearly all lesions disappeared after 7 days, as compared to no disappearance of lesions in the placebo group. All subjects treated with the composition of the present invention showed complete deactivation of the viral infection versus no de-activation in the placebo group during the follow-up period. The safety record of the drug was satisfactory; there was no difference between the composition of the present invention and the placebo in side effects or pain. Topically applied the composition of the present invention is effective in the treatment of viral induced cervical lesions.

DNA Enveloped Virus—Herpes Simplex Virus Types 1 & 2

Virus types 1 and 2 are generally responsible for upper body (oropharyngeal, dermal, ophthalmic) and genital infections respectively. Skin and mucous membranes are entry points in which the virus multiples and causes painful vesicles; infection is caused by direct contact with infected secretions. The viruses lie dormant in nerve tissue and reactivation may occur, triggered by a variety of events such as colds, menstruation, etc. The majority of the adult population is infected, with an estimated 1 minion new cases of sexually transmitted disease every year in the USA alone.

Test Results

Herpes Simplex Virus Type 1—Case Example

Several subjects with irregular, recurrent herpes infections of the lips were treated with oral application of the composition at the onset of an outbreak. The characteristic vesicles disappeared quickly and all patients have remained asymptomatic with no further treatment required.

Similar or identical results as with the composition of example 1 or example 53 (see Table C) would have been achieved by using any combination of components defined in claim 1 of the present invention and/or in examples 1 to 70 of the present invention (see Table C).

Herpes Simplex Virus Type 2—Case Example

The efficacy of the composition on the Herpes simplex 2 virus was performed on female subject who suffered recurrent instances of genital herpes at the beginning of every menstrual cycle for 10 years. Existing treatment consisted of Zovirax 7-10 days on a monthly basis, which had proved to be ineffective. The composition was administered orally under medical supervision, 300 mg thrice daily for three days, commencing 24 hours before the expected onset of the next outbreak. This outbreak was prevented. Although the composition of the present invention was not administered the following month, no symptoms appeared and the subject has remained herpes-free for over 18 months.

Similar or identical results as with the composition of example 1 or example 53 (see Table C) would have been achieved by using any combination of components defined in claim 1 of the present invention and/or in examples 1 to 70 of the present invention (see Table C).

RNA Enveloped Virus—PRRS Virus (Porcine Reproductive and Respiratory Syndrome)

PRRS is a major cause of disease in pigs; it is present in virtually all pig herds with 100% of adults being sero-positive. The disease is characterized by abortion and stillbirths in adults and respiratory disease, diarrhoea and poor growth characteristics in piglets. There is no conventional cure and treatment consists of managing secondary bacterial infections with antibiotics.

Similar or identical results as with the composition of example 1 or example 53 (see Table C) would have been achieved by using any combination of components defined in claim 1 of the present invention and/or in examples 1 to 70 of the present invention (see Table C).

Test Results

The efficacy of the composition was tested at a pig breeding centre. The infection of the piglets with PPRS was confirmed by standard tests and observation of symptoms. Two hundred piglets were orally administered the composition 500 mg twice daily for 4 consecutive days and the results compared to non-treated control groups. The results are shown in Table 4.

TABLE 4

The results of PPRS infected piglets treated with the compostion versus to control groups
PPRS infected piglets

| | Treated with the Composition[1] | | | | Control Group Untreated | | |
|---|---|---|---|---|---|---|---|
| Group | Piglets | Virus | Death | Group | Piglets | Virus | Deaths |
| 1 | 50 | 50 | 1 | 5 | 50 | 0 | 5 |
| 2 | 50 | 50 | 1 | 6 | 50 | 0 | 3 |
| 3[2] | 50 | 50 | 0 | 7 | 50 | 0 | 4 |
| 4[2] | 50 | 50 | 0 | 8 | 50 | 0 | 5 |
| Total | 200 | 200 | 2 | | 200 | 0 | 17 |
| | | | 1% | | | | 8.5% |

[1] composition administered 1 to 2 days after birth
[2] composition administered immediately at birth
[3] After 4 days Laboratory analysis demonstrated that the piglets in the test group were PPRS-free after 4 days whereas the control animals were still infected. The results showed that the death rate was reduced from 8.5% to 1% by the administration of the composition and it was noted that the treated piglets had improved appetite and growth rates as compared to the controls.

Similar or identical results as with the composition of example 1 or example 53 (see Table C) would have been achieved by using any combination of components defined in claim 1 of the present invention and/or in examples 1 to 70 of the present invention (see Table C).

DNA Non-enveloped Virus—Canine Parvovirus

Parvovirus is a highly contagious disease and major killer of puppies. It is characterized by bloody diarrhoea and progresses rapidly, with death occurring often within 2 days. It is transmitted via infected faeces. There is no conventional cure and treatment is limited to supportive therapy such as intravenous electrolytes. Infected adult dogs often show no symptoms and high levels of maternal parvovirus antibodies in the puppies' bloodstream interfere with vaccination, rendering it ineffective for the first 2-3 weeks.

Similar or identical results as with the composition of example 1 or example 53 (see Table C) would have been achieved by using any combination of components defined in claim 1 of the present invention and/or in examples 1 to 70 of the present invention (see Table C).

Test Results

Recurrent Parvovirus outbreaks at a Belgian kennel had resulted in a death rate of over 90%. Puppies developed symptoms of the disease 10-14 days after birth and the presence of Parvovirus was determined by laboratory tests conducted by Klinische Laboratorium Herentals. The efficacy of the composition on this virus was supervised by two doctors who coordinated the treatment, which consisted of the oral administration of the composition, 500 mg twice daily for 7 days. A Veterinarian followed up the treatment. Due to the commercial nature of the kennels, a control group could not be instigated. 1 to 3 days after the beginning of treatment the symptoms had disappeared in the majority of puppies. After 7 days the puppies were tested and found to be virus-free. The results are shown in Table 5.

TABLE 5

The composition treatment of puppies Infected with Parvovirus

| Bitch | Puppies | Sick | Very Sick | Dying | Cured | Death |
|---|---|---|---|---|---|---|
| Beagle 1 | 6 | 2 | 2 | 1 | 5 | 1 |
| Dalmatian | 6 | 3 | 2 | 1 | 5 | 1 |
| Golden Retriever 1 | 7 | 0 | 7 | 0 | 7 | 0 |
| Border Collie 1 | 7 | 0 | 7 | 0 | 7 | 0 |
| Berner Senner | 3 | 3 | 0 | 0 | 3 | 0 |
| Ruw H. Teckel | 6 | 6 | 0 | 0 | 6 | 0 |
| Malterzer | 5 | 5 | 0 | 0 | 5 | 0 |
| Golden Retriever 2 | 5 | 4 | 1 | 0 | 4 | 1 |
| Golden Retriever 3 | 7 | 6 | 1 | 0 | 6 | 1 |
| Labrador 2 | 8 | 8 | 0 | 0 | 8 | 0 |
| Border Collie 2 | 7 | 6 | 1 | 0 | 6 | 1 |
| Malterzer 2 | 3 | 3 | 0 | 0 | 3 | 0 |
| Bobtail | 2 | 2 | 0 | 0 | 2 | 0 |
| Labrador 3 | 4 | 4 | 0 | 0 | 4 | 0 |
| Beagle 2 | 7 | 0 | 7 | 0 | 7 | 0 |
| Labrador 4 | 2 | 0 | 2 | 0 | 2 | 0 |
| Siberian Huski | 8 | 8 | 0 | 0 | 8 | 0 |
| Golden Retriever 4 | 5 | 4 | 1 | 0 | 4 | 1 |
| Golden Retriever 5 | 7 | 7 | 0 | 0 | 7 | 0 |
| Golden Retriever 6 | 11 | 11 | 0 | 0 | 11 | 0 |
| | 116 | 82 | 31 | 2 | 110 | 6 |
| | | | | | 95% | 5% |

Treatment of the puppies with the composition reduced the death rate from over 90% to 5%.

Similar or identical results as with the composition of example 1 or example 53 (see Table C) would have been achieved by using any combination of components defined in claim 1 of the present invention and/or in examples 1 to 70 of the present invention (see Table C).

DNA Enveloped Virus—Canine Herpes Virus

Canine Herpes Virus is a leading case of puppy deaths. It lives in the respiratory and reproductive tracts of adult dogs, which show no symptoms. It is transferred to puppies during birth and via airborne nasal secretions once born. It is very contagious and spreads rapidly through litters, causing liver damage, haemorrhages, blindness and staggering. Death occurs within 24-48 hours. There is no conventional cure and treatment aimed at supportive care. Vaccination does not exist.

Test Results

There was a high infection rate of canine Herpes virus in a breeding kennel, with over 40% of the puppies suffering from this deadly disease. In order to test the efficacy of the composition on its potential to eliminate future infections, the bitches were administered the composition before delivery of the puppies, since this disease is passed from symptom-free mother to their offspring. Approximately one week before giving birth, the mothers were orally administered the composition 500 mg twice daily for 7 days. See table 6.

TABLE 6 herpes infection rates in puppies from mothers pretreated with the composition Unlike conventional anti-virals, the composition is non toxic and an effective treatment can be achieved in days rather than in weeks or months.

| Bitch | Puppies | Birth date | Herpes free |
|---|---|---|---|
| Chow-chow | 4 | 13/feb | 4 |
| Border collie | 8 | 15/feb | 8 |
| Chi-Tzu | 4 | 15/feb | 4 |
| Jack-russel | 4 | 17/feb | 4 |
| Golden retriever | 6 | 21/feb | 6 |
| Snauzer | 10 | 22/feb | 10 |
| Total | 36 | | 36 (100%) |

Similar or identical results as with the composition of example 1 or example 53 (see Table C) would have been achieved by using any combination of components defined in claim 1 of the present invention and/or in examples 1 to 70 of the present invention (see Table C).

RNA Non-enveloped Virus—Rotavirus

The Rotaviruses are the most common cause of diarrhoea in young animals, causing a 20% death rate 7-10 days after birth. The disease is often complicated by a secondary infection with *Escherichia coli*. These viruses are also associated with a wide range of similar infections in humans, especially infants.

Test Results

A pig breeding centre in Belgium experienced an epidemic of rotavirus and over 500 piglets demonstrated severe diarrhoeal symptoms. It was expected that more than 25% would die within a week since there was no effective treatment. All of the animals were administered the composition and after 3 days, 95% of the piglets were devoid of symptoms and free of the virus.

Similar or identical results as with the composition of example 1 or example 53 (see Table C) would have been achieved by using any combination of components defined in claim 1 of the present invention and/or in examples 1 to 70 of the present invention (see Table C).

Tests Results Conclusions:

Independently of the fact that the treated viruses belonged to the RNA, DNA, enveloped or non-enveloped groups, the composition of the present invention interferes with the existing or acquired lipid envelope covering the virus and not with the virus per se; all studies indicate that the composition is capable of de-activating every type of virus in a free state.

Administration of the Composition:

The best mode administering the composition is one drop or +0.05 ml per 10 kg body weight (not including excess body fat), three times daily orally. The man skilled in the art can adapt the recommended dose per kg to the average weight of a human (50 kg). Preferably encapsulated but can be taken orally mixed with fruit juice or yoghurt, topically mixing with *macadamia*-type oil for fast skin absorption and petroleum jelly for slow topical absorption. For administering to animals composition can be mixed with the feed. Aerosol or topical application according to standard aerosol dispersions methods. Rectal or vaginal insertion of suppository with indicated dose according to standard suppository administration methods.

Process of Manufacture and Galenics:

All components are manufactured and available from a specialized open market. The purity of the components preferably has to be ≥99% and this is verified before the formulation process by gas chromatography/mass spectrometry.

Preferably the components have to be pre-blended, in equal or different parts, using a sterile blending device. The preferred temperature of manufacturing and storage of the composition is between 5 and 15 degrees Celcius.

After the pre-blending process the mixture can be added to a pharmaceutically acceptable carrier. Depending on the type of application, the ratio between the composition of the present invention and the pharmaceutically acceptable carrier can range from 5% to 90%, where 50% is the most common ratio used for practical medical applications.

The mixture can then be further processed and integrated in capsules, gels, gelules, sprays, aerosols, suppositories or other drug delivery vehicles.

The method for manufacturing the compositions of the present invention comprises the following steps:
 pre-blending the components of the present invention at a temperature comprised preferably between 5 and 15° C., obtention of a mixture,
 addition of the mixture to a diluent (a pharmaceutically acceptable carrier).

The presence of a pharmaceutically acceptable carrier is optional and depends on the type of drug delivery vehicle.

The person skilled in the art knows how to manufacture the compositions of the present invention (see the compositions of Table C).

Comparative Tests (In Vivo)

The hereunder mentioned comparative tests are aimed to establish observation(s) after 10 days on 44 female human patients by Controlled Clinical Trial on Cervical Lesions (wounds) caused by the Human Papilloma Virus (HPV) which is a double stranded DNA non enveloped virus. HPV is a virus of a similar type than Adenovirus type 6 (double stranded DNA non enveloped virus).

In order to establish the non-activity of possible placebo's to be used in the clinical trial, 44 HPV infected patients were treated with a one-time dose of Placebos compositions.

AV1-HPV refers to the composition of example 1 of the present patent application (see Table C) inoculated to human patients with HPV cervical lesions.

AV53-HPV refers to the composition of example 53 of the present patent application (see Table C) inoculated to human patients with HPV cervical lesions.

The results indicate that the treatment with the 7 Placebos had no effect on de-activation of the HPV and the subsequent regression of the lesions on the surface of the cervix (also called neck of the uterus).

The person skilled in the art knows how to perform such tests.

Results:

| Treatment | Component(s) | Percentage by weight | Observation(s) after 10 days |
|---|---|---|---|
| Placebo 1 | R-(−)-Carvone | 100% | No regression of lesions on the surface of the cervix |
| Placebo 2 | S-(+)-Carvone | 100% | No regression of lesions on the surface of the cervix |
| Placebo 3 carvone (racemate) | (R)-Carvone + (S)-Carvone | 60%-50% | No regression of lesions on the surface of the cervix |
| Placebo 4 | Trans-Geraniol | 100% | No regression of lesions on the surface of the cervix |
| Placebo 5 | (R) Carvone + Trans-Geraniol | 50%-50% | No regression of lesions on the surface of the cervix |
| Placebo 6 | (S) Carvone + Trans-Geraniol | 50%-50% | No regression of lesions on the surface of the cervix |
| Placebo 7 | Carvone (racemate) + Trans-Geraniol | 50%-50% | No regression of lesions on the surface of the cervix |
| Placebo 8 | Eugenol | 100% | No regression of lesions on the surface of the cervix |
| Placebo 9 | Trans Nerolidol | 100% | No regression of lesions on surface of the cervix |
| Placebo 10 | Eugenol + Carvone (racemate) | 50%-50% | No regression of lesions on the surface of the cervix |
| Placebo 11 | Eugeniol + Trans Geraniol | 50%-50% | No regression of lesions on the surface of the cervix |
| Placebo 12 | Eugenol + Trans Nerolidol | 50%-50% | No regression of lesions on the surface of the cervix |
| Placebo 13 | Eugenol + Carvone (racemate) + trans Nerolidol | 33.33%-33.33%-33.33% | No regression of lesions on the surface of the cervix |
| Placebo 15 | Eugenol + Trans Geraniol + Trans Nerolidol | 33.33%-33.33%-33.33% | No regression of lesions on the surface of the cervix |
| Placebo 16 | Eugenol methyl ether | 100% | No regression of lesions on the surface of the cervix |
| Placebo 17 | Linalooloxide | 100% | No regression of lesions on the surface of the cervix |
| Placebo 18 | (cis+trans)-1,2-(+)-Limonene oxide | 100% | No regression of lesions on the surface of the cervix |
| Placebo 19 | (+/−)-Isomenthol | 100% | No regression of lesions on the surface of the cervix |

| Treatment | Component(s) | Percentage by weight | Observation(s) after 10 days |
|---|---|---|---|
| Placebo 20 | (cis/trans) Nerolidol | 100% | No regression of lesions on the surface of the cervix |
| Placebo 21 | Lavendulol | 100% | No regression of lesions on the surface of the cervix |
| Placebo 22 | Eugenol methyl ether + Linalooloxide + (cis+trans)-1,2-(+)-Limonene oxide + (+/−)-Isomenthol + Eugenol | 20% 20% 20% 20% 20% | No regression of lesions on the surface of the cervix |
| Placebo 23 | (cis/trans) Nerolidol + Eugenol | 50% each | No regression of lesions on the surface of the cervix |
| Placebo 24 | Lavendulol + Eugenol | 50% each | No regression of lesions on the surface of the cervix |
| AV1-HPV | See the composition of Examplee 1 (on the page following this table) | 100% in total | Between 30-100% regression of lesions on the surface of the cervix |
| AV53-HPV | See the composition of Example 53 (on the Page following this table) | 100% in total | Between 30-100% regression of lesions on the surface of the cervix |
| AV56-HPV | See the composition of Example 56 (on the page following this table) | 100% in total | Between 20-100% regression of lesions on the surface of the cervix |
| AV57-HPV | See the composition of Example 57 (on the page following this table) | 100% in total | Between 20-100% regression of lesions on the surface of the cervix |
| AV58-HPV | See the composition of Example 58 (on the page following this table) | 100% in total | Between 20-100% regression of lesions on the surface of the cervix |
| AV59-HPV | See the composition of Example 59 (on the page following this table) | 100% in total | Between 20-100% regression of lesions on the surface of the cervix |
| AV60-HPV | See the composition of Example 60 (on the page following this table) | 100% in total | Between 20-100% regression of lesions on the surface of the cervix |
| AV61-HPV | See the composition of Example 61 (on the page following this table) | 100% in total | Between 20-100% regression of lesions on the surface of the cervix |
| AV62-HPV | See the composition of Example 62 (on the page following this table) | 100% in total | Between 20-100% regression of lesions on the surface of the cervix |
| AV63-HPV | See the composition of Example 63 (on the page following this table) | 100% in total | Between 20-100% regression of lesions on the surface of the cervix |
| AV64-HPV | See the composition of Example 64 (on the page following this table) | 100% in total | Between 20-100% regression of lesions on the surface of the cervix |
| AV65-HPV | See the composition of Example 65 (on the page following this table) | 100% in total | Between 20-100% regression of lesions on the surface of the cervix |
| AV66-HPV | See the composition of Example 66 (on the page following this table) | 100% in total | Between 20-100% regression of lesions on the surface of the cervix |
| AV67-HPV | See the composition of Example 67 (on the page following this table) | 100% in total | Between 20-100% regression of lesions on the surface of the cervix |
| AV68-HPV | See the composition of Example 68 (on the page following this table) | 100% in total | Between 20-100% regression of lesions on the surface of the cervix |

-continued

| Treatment | Component(s) | Percentage by weight | Observation(s) after 10 days |
|---|---|---|---|
| AV69-HPV | See the composition of Example 69 (on the page following this table) | 100% in total | Between 20-100% regression of lesions on the surface of the cervix |
| AV70-HPV | See the composition of Example 70 (on the page following this table) | 100% in total | Between 20-100% regression of lesions on the surface of the cervix |

| Treatment | Component(s) | Percentage by weight |
|---|---|---|
| AV53-HPV | Composition of Example 53 (see table C) contains: | |
|  | R-(−)-2-methyl-5-(prop-1-en-2-yl)-cyclohex-2-enone (R)-Carvone | 12.5% |
|  | S-(+)-2-methyl-5-(prop-1-en-2-yl)-cyclohex-2-enone (S)-Carvone | 12.5% |
|  | (2E)-3,7-dimethylocta-2,6-dien-1-ol Trans-Geraniol | 25% |
|  | 2-methoxy-4-prop-2-enylphenol Eugenol | 25% |
|  | (6E)-3,7,11-trimethyldodeca-1,6,10-trien-3-ol Trans-Nerolidol | 25% |
| AV1-HPV | Composition of Example 1 (see table C) contains: | |
|  | Eugenol methylether | 12.5% |
|  | Linalooloxide | 12.5% |
|  | (cis+trans)-1,2-(+)-Limonene oxide | 12.5% |
|  | (+/−)-Isomenthol | 12.5% |
|  | (−)-Carvone | 12.5% |
|  | Trans-Geraniol | 12.5% |
|  | Eugenol | 12.5% |
|  | (+)-Carvone | 12.5% |
| AV56-HPV | Composition of Example 56 (see table C) contains: | |
|  | (−)-Carvone | 10% |
|  | (+)-Carvone | 10% |
|  | Trans-Geraniol | 10% |
|  | combined with the 128 components listed in list A | 0.54% for each component |
| AV57-HPV | Composition of Example 57 (see table C) contains: | |
|  | (−)-Carvone | 10% |
|  | (+)-Carvone | 10% |
|  | Trans-Geraniol | 10% |
|  | combined with the 64 first components listed in list A | 1.29% for each component |
| AV58-HPV | Composition of Example 58 (see table C) contains: | |
|  | (−)-Carvone | 10% |
|  | (+)-Carvone | 10% |
|  | Trans-Geraniol | 10% |
|  | combined with the 64 last components listed in list A (i.e. the 65th to the 128th components) | 1.29% for each component |
| AV59-HPV | Composition of Example 59 (see table C) contains: | |
|  | (−)-Carvone | 10% |
|  | (+)-Carvone | 10% |
|  | Trans-Geraniol | 10% |
|  | combined with the 32 first components listed in list A | 2.18% for each component |
| AV60-HPV | Composition of Example 60 (see table C) contains: | |
|  | (−)-Carvone | 10% |
|  | (+)-Carvone | 10% |
|  | Trans-Geraniol | 10% |

| Treatment | Component(s) | Percentage by weight |
|---|---|---|
| | combined with the 32 last components listed in list A (i.e. the 97th to the 128th components) | 2.18% for each component |
| AV61-HPV | Composition of Example 61 (see table C) contains: | |
| | (−)-Carvone | 10% |
| | (+)-Carvone | 10% |
| | Trans-Geraniol | 10% |
| | combined with the 16 first components listed in list A | 4.37% for each component |
| AV62-HPV | Composition of Example 62 (see table C) contains: | |
| | (−)-Carvone | 10% |
| | (+)-Carvone | 10% |
| | Trans-Geraniol | 10% |
| | combined with the 16 last components listed in list A (i.e. the 112th to the 128th components) | 4.37% for each component |
| AV63-HPV | Composition of Example 63 (see table C) contains: | |
| | (−)-Carvone | 10% |
| | (+)-Carvone | 10% |
| | Trans-Geraniol | 10% |
| | combined with the 8 first components listed in list A | 8.75% for each component |
| AV64-HPV | Composition of Example 64 (see table C) contains: | |
| | (−)-Carvone | 10% |
| | (+)-Carvone | 10% |
| | Trans-Geraniol | 10% |
| | combined with the 8 last components listed in list A (i.e. the 121th to the 128th components) | 8.75% for each component |
| AV65-HPV | Composition of Example 65 (see table C) contains: | |
| | (−)-Carvone | 14.28% |
| | (+)-Carvone | 14.28% |
| | Trans-Geraniol | 14.28% |
| | combined with the 4 first components listed in list A | 14.28% for each component |
| AV66-HPV | Composition of Example 66 (see table C) contains: | |
| | (−)-Carvone | 14.28% |
| | (+)-Carvone | 14.28% |
| | Trans-Geraniol | 14.28% |
| | combined with the 4 last components listed in list A (i.e. the 125th to the 128th components) | 14.28% for each component |
| AV67-HPV | Composition of Example 67 (see table C) contains: | |
| | (−)-Carvone | 20% |
| | (+)-Carvone | 20% |
| | Trans-Geraniol | 20% |
| | combined with the 2 first components listed in list A | 20% for each component |
| AV68-HPV | Composition of Example 68 (see table C) contains: | |
| | (−)-Carvone | 20% |
| | (+)-Carvone | 20% |
| | Trans-Geraniol | 20% |
| | combined with the 2 last components listed in list A (i.e. the 127th to the 128th components) | 20% for each component |
| AV69-HPV | Composition of Example 69 (see table C) contains: | |
| | (−)-Carvone | 25% |
| | (+)-Carvone | 25% |
| | Trans-Geraniol | 25% |
| | combined with the first component listed in list A: (−)-alpha-Pinene | 25% for each component |
| AV70-HPV | Composition of Example 70 (see table C) contains: | |
| | (−)-Carvone | 25% |
| | (+)-Carvone | 25% |

-continued

| Treatment | Component(s) | Percentage by weight |
|---|---|---|
| | Trans-Geraniol combined with the 128th component listed in list A: Linalooloxide | 25% 25% for each component |

Important Note:

The percentage of regression of the lesions observed on the surface of the cervix (i.e. between 20-100%) applies to composition(s) containing:

(+)-Carvone+(−)-Carvone+Trans-Geraniol in combination with at least one more component selected from the list of claim 1 (essential oils components of list A).

The specific examples for proving that all components of claim 1 are comprised within the scope of the present invention are those mentioned in examples 56, 57, 58, 59, 60, 61, 62, 63, 64, 65, 66, 67, 68, 69 and 70 (see Table C and the corresponding percentages by weight mentioned previously).

The results of example 1 and example 53 (i.e. between 30-100% regression of lesions on the surface of the cervix) are even better than those of examples 56 to 70 (corresponding to list A) (i.e. between 20-100% regression of lesions on the surface of the cervix).

No regression of lesions on the surface of the cervix have been observed (for placebo's compositions 1 to 24).

Dilution:

The Placebo's and the composition(s) of the present invention can also be diluted in using Biological Virgin Oil (50% by weight of virgin olive oil) to enable more even application to the Cervix.

The results obtained for the diluted composition(s) of the present invention mentioned previously are:
- between 30-100% regression of lesions on the surface of the cervix for the diluted composition of example 1 or example 53.
- between 20-100% regression of the lesions observed on the surface of the cervix (for diluted composition of examples 56 to 70 (see list A).
- no regression of lesions on the surface of the cervix (for diluted placebo's compositions 1 to 24).

Conclusion:

A synergism therefore exists between (+)carvone and (−)carvone and trans-geraniol and additional essential oils component(s) of the present composition(s).

There is a surprising and unexpected effect (in terms of regression of lesions on the surface of the cervix) to use the pure or diluted composition(s) of the present invention compared to the pure or diluted placebo compositions 1 to 24.

Placebo Examples for Making the Comparative Tests: Table B:

Placebo's given in the following comparative tests contained either 1 component (3 times 33.33%=100% wt) or a combination of 3 different components each in an amount of 33.33% by weight, except for example 55 having 4 different components, each in an amount of 25% by weight.

TABLE B

Placebo Examples

| | Component | % | Component | % | Component | % |
|---|---|---|---|---|---|---|
| Placebo Example 1 | (+)-Camphor | 33.33% | (−)-Fenchone | 33.33% | (+)-Neomenthol | 33.33% |
| Placebo Example 2 | 1,8-Cineole | 33.33% | (+)-Isopinocampheol | 33.33% | R-(+)-Pulegone | 33.33% |
| Placebo Example 3 | Camphene | 33.33% | (+)-Fenchone | 33.33% | beta-Naphthol | 33.33% |
| Placebo Example 4 | trans-Nerolidol | 33.33% | trans-Nerolidol | 33.33% | trans-Nerolidol | 33.33% |
| placebo Example 5 | beta-Thujaplicin | 33.33% | Linalool | 33.33% | (−)-Verbenone | 33.33% |
| Placebo Example 6 | (−)-Carveol | 33.33% | Heptyl acetate | 33.33% | Nootkatone | 33.33% |
| Placebo Example 8 | (+/−)-Camphor | 33.33% | Furfuryl acetate | 33.33% | (+/−)-Neomenthol | 33.33% |
| Placebo Example 9 | Acetic acid methylester | 33.33% | (+)-Cuparene | 33.33% | Linalool | 33.33% |
| Placebo Example 10 | Geraniol | 33.33% | (+)-Carvone | 33.33% | (−)-Carvone | 33.33% |
| Placebo Example 11 | (+)-Borneol | 33.33% | (−)-Dihydrocarvyl acetate | 33.33% | (+/−)-Menthol | 33.33% |
| Placebo Example 12 | Tetrahydrolinalool | 33.33% | Estragole | 33.33% | (+)-Fenchone | 33.33% |
| Placebo Example 13 | p-Allylanisole | 33.33% | Cypress camphor | 33.33% | Linalyl acetate | 33.33% |
| Placebo Example 14 | Azulene | 33.33% | Dihydrocarveol | 33.33% | 4-Menthan-3-one | 33.33% |
| Placebo Example 15 | (−)-Verbenone | 33.33% | alpha-Humulene | 33.33% | 2-Norbornanone | 33.33% |
| Placebo Example 16 | (−)-Camphor | 33.33% | Furfuryl alcohol | 33.33% | Nerol | 33.33% |
| Placebo Example 17 | 3-Carene | 33.33% | Geranyl acetate | 93.33% | cis-Nerolidol | 33.33% |

TABLE B-continued

| | Placebo Examples | | | | | |
|---|---|---|---|---|---|---|
| | Component | % | Component | % | Component | % |
| Placebo Example 18 | alpha-Caryophyllene | 33.33% | alpha-Ionone | 33.33% | 3-Octanone | 33.33% |
| Placebo Example 19 | 1,4-Cineole | 33.33% | Isomenthone | 33.33% | Piperitone | 33.33% |
| Placebo Example 20 | Eugenol | 33.33% | Eugenol | 33.33% | Eugenol | 33.33% |
| Placebo Example 20 | Eugenol | 33.33% | Eugenol | 33.33% | Eugenol | 33.33% |
| Placebo Example 21 | Benzoic acid eugenylester | 33.33% | (+)-Dihydrocarveol | 33.33% | (−)-Menthol | 33.33% |
| Placebo Example 22 | Terpinyl acetate | 33.33% | (+)-2-Carene | 33.33% | farnesol | 33.33% |
| Placebo Example 23 | (−)-Bornyl acetate | 33.33% | Estragole | 33.33% | (−)-Menthone | 33.33% |
| Placebo Example 24 | (−)-Carvone | 33.33% | (−)-Carvone | 33.33% | (−)-Carvone | 33.33% |
| Placebo Example 25 | Butyl acetate | 33.33% | Eucalyptol | 33.33% | (−)-Menthyl acetate | 33.33% |
| Placebo Example 26 | Citral | 33.33% | 2-Isopropyl-5-methylphenol | 33.33% | Sabinyl acetate | 33.33% |
| Placebo Example 27 | Cajeputol | 33.33% | Eugenylbenzoate | 33.33% | (−)-trans-Myrtanol | 33.33% |
| Placebo Example 28 | Linalool oxide | 33.33% | Linalool oxide | 33.33% | Linalool oxide | 33.33% |
| Placebo Example 29 | Lavendulol | 33.33% | Lavendulol | 33.33% | Lavendulol | 33.33% |
| Placebo Example 30 | (−)-Borneol | 33.33% | Dillapiole | 33.33% | (+/−)-Menthol | 33.33% |
| Placebo Example 31 | alpha-Cedrene | 33.33% | Isobutyl acetate | 33.33% | (1S,2S)-10-Pinanol | 33.33% |
| Placebo Example 32 | Chamazulen | 33.33% | Isoeugenylacetate | 33.33% | (+/−)-alpha-Pinene | 33.33% |
| Placebo Example 33, 33 | Acetic acid butylester | 33.33% | (+)-Citronellol | 33.33% | S-(−)-Limonene | 33.33% |
| Placebo Example 34 | (+)-Carvone | 33.33% | (+)-Carvone | 33.33% | (+)-Carvone | 33.33% |
| Placebo Example 35 | (cis + trans)-Nerolidol | 33.33% | (cis + trans)-Nerolidol | 33.33% | (cis + trans)-Nerolidol | 33.33% |
| Placebo Example 36 | (−)-Caryophyllene oxide | 33.33% | Isobornyl acetate | 33.33% | (−)-Perillylalcohol | 33.33% |
| Placebo Example 37 | Eugenol methylether | 33.33% | Eugenol methylether | 33.33% | Eugenol methylether | 33.33% |
| Placebo Example 38 | Cedar camphor | 33.33% | Isobornyl isovalerate | 33.33% | R-(−)-alpha-Phellandrene | 33.33% |
| Placebo Example 39 | Cedrol | 33.33% | Isoeugenol | 33.33% | (−)-alpha-Pinene | 33.33% |
| Placebo Example 40 | beta-Cedrene | 33.33% | Isocineole | 33.33% | (+)-alpha-Pinene | 33.33% |
| Placebo Example 41 | (+)-Isomenthol | 33.33% | (+)-Isomenthol | 33.33% | (+)-Isomenthol | 33.33% |
| Placebo Example 42 | (−)-Citronellol | 33.33% | Isothymol | 33.33% | alpha-Terpinene | 33.33% |
| Placebo Example 43 | Geraniol | 33.33% | Geraniol | 33.33% | Geraniol | 33.33% |
| Placebo Example 44 | (−)-Citronellal | 33.33% | (−)-Isopulegol | 33.33% | trans-Stilbene | 33.33% |
| Placebo Example 45 | (1R)-Chrysanthemolactone | 33.33% | Isolongifolene | 33.33% | (−)-beta-Pinene | 33.33% |
| Placebo Example 46 | exo-2-Camphanol | 33.33% | Farnesol | 33.33% | (−)-Myrtenol | 33.33% |
| Placebo Example 47 | Cinnamyl acetate | 33.33% | (−)-Isopinocampheol | 33.33% | Sabinene | 33.33% |
| Placebo Example 48 | (+/−)-beta-Citronellol | 33.33% | cis-Jasmone | 33.33% | gamma-Terpinene | 33.33% |
| Placebo Example 49 | Terpinolene | 33.33% | Lemonol | 33.33% | alpha-Terpineol | 33.33% |
| Placebo Example 50 | Acetic acid cinnamylester | 33.33% | Citronellol | 33.33% | R-(+)-Limonene | 33.33% |
| Placebo Example 51 | Acetic acid isobutylester | 33.33% | Cuminaldehyde | 33.33% | (−)-Linalool | 33.33% |
| Placebo Example 52 | (cis + Trans)-1,2(+)-limonene oxide | 33.33% | (cis + Trans)-1,2(+)-limonene oxide | 33.33% | (cis + Trans)-1,2(+)-limonene oxide | 33.33% |
| Placebo Example 53 | alpha-(−)-Bisabolol | 33.33% | (+)-Dihydrocarvone | 33.33% | (+)-Menthol | 33.33% |

TABLE B-continued

Placebo Examples

| Component | % | Component | % | Component | % |
|---|---|---|---|---|---|
| Placebo Example 54 | Acetic acid heptylester | 33.33% | DL-Citronellyl acetate | 33.33% | (+/−)-Linalool | 33.33% |
| Placebo example 55: | Eugenol methylether (25% wt) + Linalooloxide (25% wt) + (cis + trans)-1,2(+)-limonene oxide (25% wt) + (+)-isomenthol (25% wt). | | | | | |

All following comparative tests have been performed by using essential oils components having the following percentages by weight:

Examples 1 to 52 of Table C contain 12.5% by weight of each component.

Examples 53 to 55 of Table C contain 20% by weight of each component.

The components of examples 56 to 70 of Table C contain the following percentages by weight:

| Component(s) | Percentage by weight |
|---|---|
| Composition of Example 56 (see table C) contains: | |
| (−)-Carvone | 10% |
| (+)-Carvone | 10% |
| Trans-Geraniol | 10% |
| combined with the 128 components listed in list A | 0.54% for each component |
| Composition of Example 57 (see table C) contains: | |
| (−)-Carvone | 10% |
| (+)-Carvone | 10% |
| Trans-Geraniol | 10% |
| combined with the 64 first components listed in list A | 1.29% for each component |
| Composition of Example 58 (see table C) contains: | |
| (−)-Carvone | 10% |
| (+)-Carvone | 10% |
| Trans-Geraniol | 10% |
| combined with the 64 last components listed in list A (i.e. the 65th to the 128th components) | 1.29% for each component |
| Composition of Example 59 (see table C) contains: | |
| (−)-Carvone | 10% |
| (+)-Carvone | 10% |
| Trans-Geraniol | 10% |
| combined with the 32 first components listed in list A | 2.18% for each component |
| Composition of Example 60 (see table C) contains: | |
| (−)-Carvone | 10% |
| (+)-Carvone | 10% |
| Trans-Geraniol | 10% |
| combined with the 32 last components listed in list A (i.e. the 97th to the 128th components) | 2.18% for each component |
| Composition of Example 61 (see table C) contains: | |
| (−)-Carvone | 10% |
| (+)-Carvone | 10% |
| Trans-Geraniol | 10% |
| combined with the 16 first components listed in list A | 4.37% for each component |
| Composition of Example 62 (see table C) contains: | |
| (−)-Carvone | 10% |
| (+)-Carvone | 10% |
| Trans-Geraniol | 10% |
| combined with the 16 last components listed in list A (i.e. the 112th to the 128th components) | 4.37% for each component |
| Composition of Example 63 (see table C) contains: | |
| (−)-Carvone | 10% |
| (+)-Carvone | 10% |
| Trans-Geraniol | 10% |
| combined with the 8 first components listed in list A | 8.75% for each component |
| Composition of Example 64 (see table C) contains: | |
| (−)-Carvone | 10% |
| (+)-Carvone | 10% |
| Trans-Geraniol | 10% |
| combined with the 8 last components listed in list A (i.e. the 121th to the 128th components) | 8.75% for each component |
| Composition of Example 65 (see table C) contains: | |
| (−)-Carvone | 14.28% |
| (+)-Carvone | 14.28% |
| Trans-Geraniol | 14.28% |
| combined with the 4 first components listed in list A | 14.28% for each component |
| Composition of Example 66 (see table C) contains: | |
| (−)-Carvone | 14.28% |
| (+)-Carvone | 14.28% |
| Trans-Geraniol | 14.28% |
| combined with the 4 last components listed in list A (i.e. the 125th to the 128th components) | 14.28% for each component |
| Composition of Example 67 (see table C) contains: | |
| (−)-Carvone | 20% |
| (+)-Carvone | 20% |
| Trans-Geraniol | 20% |
| combined with the 2 first components listed in list A | 20% for each component |
| Composition of Example 68 (see table C) contains: | |
| (−)-Carvone | 20% |
| (+)-Carvone | 20% |
| Trans-Geraniol | 20% |
| combined with the 2 last components listed in list A (i.e. the 127th to the 128th components) | 20% for each component |
| Composition of Example 69 (see table C) contains: | |
| (−)-Carvone | 25% |
| (+)-Carvone | 25% |
| Trans-Geraniol | 25% |
| combined with the first component listed in list A: (−)-alpha-Pinene | 25% for each component |
| Composition of Example 70 (see table C) contains: | |
| (−)-Carvone | 25% |
| (+)-Carvone | 25% |
| Trans-Geraniol | 25% |

| Component(s) | Percentage by weight |
|---|---|
| combined with the 128th component listed in list A: Linalooloxide | 25% for each component |

RNA Enveloped Virus—PRRS Virus (Porcine Reproductive and Respiratory Syndrome)

An in vivo comparative study was done at a pig breeding center. The infection of the piglets with PPRS was confirmed by standard tests and observation of symptoms. 55 piglets were orally administered with 70 alternative compositions (compositions of examples 1-70 of table C) 50 to 200 mg twice daily for 2 to 5 consecutive days and the results are compared to 55 other piglets who received the placebo compositions of table B. 200 mg for 5 days.

Veterinary diagnosis combined with Laboratory analysis demonstrated that the piglets in the test group were PPRS-free after 2 to 5 days, whereas the piglets that received the placebo did not show any signs of improvement after 5 days.

The man skilled in the art knows how to perform such tests.

| PPRS infected piglets - RNA Enveloped | | | | | |
|---|---|---|---|---|---|
| Treated with the Compositions of Table C | | | Placebo of Table B | | |
| Composition of the present invention | Dosage | Virus free | Placebo of table B Used | Dosage | Virus free after 5 days |
| Composition Example 1 | 50 mg | 2 days | Placebo Example 1 | 200 mg | None |
| Composition Example 2 | 200 mg | 4 days | Placebo Example 2 | 200 mg | None |
| Composition Example 3 | 200 mg | 4 days | Placebo Example 3 | 200 mg | None |
| Composition Example 4 | 200 mg | 4 days | Placebo Example 4 | 200 mg | None |
| Composition Example 5 | 200 mg | 5 days | Placebo Example 5 | 200 mg | None |
| Composition Example 6 | 200 mg | 5 days | Placebo Example 6 | 200 mg | None |
| Composition Example 7 | 200 mg | 4 days | | | |
| Composition Example 8 | 200 mg | 4 days | Placebo Example 8 | 200 mg | None |
| Composition Example 9 | 200 mg | 4 days | Placebo Example 9 | 200 mg | None |
| Composition Example 10 | 200 mg | 5 days | Placebo Example 10 | 200 mg | None |
| Composition Example 11 | 200 mg | 4 days | Placebo Example 11 | 200 mg | None |
| Composition Example 12 | 200 mg | 4 days | Placebo Example 12 | 200 mg | None |
| Composition Example 13 | 200 mg | 4 days | Placebo Example 13 | 200 mg | None |
| Composition Example 14 | 200 mg | 5 days | Placebo Example 14 | 200 mg | None |
| Composition Example 15 | 200 mg | 5 days | Placebo Example 15 | 200 mg | None |
| Composition Example 16 | 200 mg | 5 days | Placebo Example 16 | 200 mg | None |
| Composition Example 17 | 200 mg | 4 days | Placebo Example 17 | 200 mg | None |
| Composition Example 18 | 200 mg | 5 days | Placebo Example 18 | 200 mg | None |
| Composition Example 19 | 200 mg | 4 days | Placebo Example 19 | 200 mg | None |
| Composition Example 20 | 200 mg | 4 days | Placebo Example 20 | 200 mg | None |
| Composition Example 21 | 200 mg | 4 days | Placebo Example 21 | 200 mg | None |
| Composition Example 22 | 200 mg | 4 days | Placebo Example 22 | 200 mg | None |
| Composition Example 23 | 200 mg | 4 days | Placebo Example 23 | 200 mg | None |
| Composition Example 24 | 200 mg | 4 days | Placebo Example 24 | 200 mg | None |
| Composition Example 25 | 200 mg | 4 days | Placebo Example 25 | 200 mg | None |
| Composition Example 26 | 200 mg | 4 days | Placebo Example 26 | 200 mg | None |
| Composition Example 27 | 200 mg | 4 days | Placebo Example 27 | 200 mg | None |
| Composition Example 28 | 200 mg | 4 days | Placebo Example 28 | 200 mg | None |
| Composition Example 29 | 200 mg | 4 days | Placebo Example 29 | 200 mg | None |
| Composition Example 30 | 200 mg | 4 days | Placebo Example 30 | 200 mg | None |
| Composition Example 31 | 200 mg | 4 days | Placebo Example 31 | 200 mg | None |
| Composition Example 32 | 200 mg | 4 days | Placebo Example 32 | 200 mg | None |
| Composition Example 33 | 200 mg | 4 days | Placebo Example 33 | 200 mg | None |
| Composition Example 34 | 200 mg | 4 days | Placebo Example 34 | 200 mg | None |
| Composition Example 35 | 200 mg | 5 days | Placebo Example 35 | 200 mg | None |
| Composition Example 36 | 200 mg | 5 days | Placebo Example 36 | 200 mg | None |
| Composition Example 37 | 200 mg | 4 days | Placebo Example 37 | 200 mg | None |
| Composition Example 38 | 200 mg | 4 days | Placebo Example 38 | 200 mg | None |
| Composition Example 39 | 200 mg | 4 days | Placebo Example 39 | 200 mg | None |
| Composition Example 40 | 200 mg | 4 days | Placebo Example

| PPRS infected piglets - RNA Enveloped ||||||
|---|---|---|---|---|---|
| Treated with the Compositions of Table C |||Placebo of Table B ||
| Composition of the present invention | Dosage | Virus free | Placebo of table B Used | Dosage | Virus free after 5 days |
| Composition Example 41 | 200 mg | 4 days | Placebo Example 41 | 200 mg | None |
| Composition Example 42 | 200 mg | 4 days | Placebo Example 42 | 200 mg | None |
| Composition Example 43 | 200 mg | 4 days | Placebo Example 43 | 200 mg | None |
| Composition Example 44 | 200 mg | 4 days | Placebo Example 44 | 200 mg | None |
| Composition Example 45 | 200 mg | 4 days | Placebo Example 45 | 200 mg | None |
| Composition Example 46 | 200 mg | 4 days | Placebo Example 46 | 200 mg | None |
| Composition Example 47 | 200 mg | 4 days | Placebo Example 47 | 200 mg | None |
| Composition Example 48 | 200 mg | 4 days | Placebo Example 48 | 200 mg | None |
| Composition Example 49 | 200 mg | 4 days | Placebo Example 49 | 200 mg | None |
| Composition Example 50 | 200 mg | 4 days | Placebo Example 50 | 200 mg | None |
| Composition Example 51 | 200 mg | 4 days | Placebo Example 51 | 200 mg | None |
| Composition Example 52 | 200 mg | 5 days | Placebo Example 52 | 200 mg | None |
| Composition Example 53 | 200 mg | 3 days | Placebo Example 53 | 200 mg | None |
| Composition Example 54 | 50 mg | 2 days | Placebo Example 54 | 200 mg | None |
| Composition Example 55 | 200 mg | 4 days | Placebo Example 55 | 200 mg | None |
| Composition Example 56 | 200 mg | 4 days | Placebo Example 10 | 200 mg | None |
| Composition Example 57 | 200 mg | 4 days | Placebo Example 10 | 200 mg | None |
| Composition Example 58 | 200 mg | 4 days | Placebo Example 10 | 200 mg | None |
| Composition Example 59 | 200 mg | 4 days | Placebo Example 10 | 200 mg | None |
| Composition Example 60 | 200 mg | 4 days | Placebo Example 10 | 200 mg | None |
| Composition Example 61 | 200 mg | 4 days | Placebo Example 10 | 200 mg | None |
| Composition Example 62 | 200 mg | 4 days | Placebo Example 10 | 200 mg | None |
| Composition Example 63 | 200 mg | 4 days | Placebo Example 10 | 200 mg | None |
| Composition Example 64 | 200 mg | 4 days | Placebo Example 10 | 200 mg | None |
| Composition Example 65 | 200 mg | 4 days | Placebo Example 10 | 200 mg | None |
| Composition Example 66 | 200 mg | 4 days | Placebo Example 10 | 200 mg | None |
| Composition Example 67 | 200 mg | 4 days | Placebo Example 10 | 200 mg | None |
| Composition Example 68 | 200 mg | 4 days | Placebo Example 10 | 200 mg | None |
| Composition Example 69 | 200 mg | 4 days | Placebo Example 10 | 200 mg | None |
| Composition Example 70 | 200 mg | 4 days | Placebo Example 10 | 200 mg | None |

RNA Non-enveloped Virus—Rotavirus

An in vivo comparative test was done in a Pig breeding center on 55 Piglets infected with ROTAVIRUS. All piglets experienced severe diarrhea.

55 Piglets received each individually an alternative composition of between 50 mg and 200 mg of the list of alternative compositions Examples 1 to 70 (see the composition listed in Table C). After 2 to 3 days none of the Piglets experienced any diarrhea.

The 55 other piglets of the Placebo group were given 200 mg each individually composition of Placebo Components listed in table B. After 3 days all the Piglets of the placebo group still experienced diarrhea.

The man skilled in the art knows how to perform such tests.

| Rota Virus - RNA Non Enveloped ||||||
|---|---|---|---|---|---|
| Treated with the Compositions of Table C |||Placebo of Table B ||
| Composition of the present invention | Dosage | Virus free | Placebo of table B Used | Dosage | Virus free after 3 days |
| Composition Example 1 | 50 mg | 2 days | Placebo Example 1 | 200 mg | None |
| Composition Example 2 | 200 mg | 3 days | Placebo Example 2 | 200 mg | None |
| Composition Example 3 | 200 mg | 3 days | Placebo Example 3 | 200 mg | None |
| Composition Example 4 | 200 mg | 3 days | Placebo Example 4 | 200 mg | None |
| Composition Example 5 | 200 mg | 3 days | Placebo Example 5 | 200 mg | None |
| Composition Example 6 | 200 mg | 3 days | Placebo Example 6 | 200 mg | None |
| Composition Example 7 | 200 mg | 3 days | | | |
| Composition Example 8 | 200 mg | 3 days | Placebo Example 8 | 200 mg | None |
| Composition Example 9 | 200 mg | 3 days | Placebo Example 9 | 200 mg | None |
| Composition Example 10 | 200 mg | 3 days | Placebo Example 10 | 200 mg | None |

Rota Virus - RNA Non Enveloped

| Treated with the Compositions of Table C | | | Placebo of Table B | | |
|---|---|---|---|---|---|
| Composition of the present invention | Dosage | Virus free | Placebo of table B Used | Dosage | Virus free after 3 days |
| Composition Example 11 | 200 mg | 3 days | Placebo Example 11 | 200 mg | None |
| Composition Example 12 | 200 mg | 3 days | Placebo Example 12 | 200 mg | None |
| Composition Example 13 | 200 mg | 3 days | Placebo Example 13 | 200 mg | None |
| Composition Example 14 | 200 mg | 3 days | Placebo Example 14 | 200 mg | None |
| Composition Example 15 | 200 mg | 3 days | Placebo Example 15 | 200 mg | None |
| Composition Example 16 | 200 mg | 3 days | Placebo Example 16 | 200 mg | None |
| Composition Example 17 | 200 mg | 3 days | Placebo Example 17 | 200 mg | None |
| Composition Example 18 | 200 mg | 3 days | Placebo Example 18 | 200 mg | None |
| Composition Example 19 | 200 mg | 3 days | Placebo Example 19 | 200 mg | None |
| Composition Example 20 | 200 mg | 3 days | Placebo Example 20 | 200 mg | None |
| Composition Example 21 | 200 mg | 3 days | Placebo Example 21 | 200 mg | None |
| Composition Example 22 | 200 mg | 3 days | Placebo Example 22 | 200 mg | None |
| Composition Example 23 | 200 mg | 3 days | Placebo Example 23 | 200 mg | None |
| Composition Example 24 | 200 mg | 3 days | Placebo Example 24 | 200 mg | None |
| Composition Example 25 | 200 mg | 3 days | Placebo Example 25 | 200 mg | None |
| Composition Example 26 | 200 mg | 3 days | Placebo Example 26 | 200 mg | None |
| Composition Example 27 | 200 mg | 3 days | Placebo Example 27 | 200 mg | None |
| Composition Example 28 | 200 mg | 3 days | Placebo Example 28 | 200 mg | None |
| Composition Example 29 | 200 mg | 3 days | Placebo Example 29 | 200 mg | None |
| Composition Example 30 | 200 mg | 3 days | Placebo Example 30 | 200 mg | None |
| Composition Example 31 | 200 mg | 3 days | Placebo Example 31 | 200 mg | None |
| Composition Example 32 | 200 mg | 3 days | Placebo Example 32 | 200 mg | None |
| Composition Example 33 | 200 mg | 3 days | Placebo Example 33 | 200 mg | None |
| Composition Example 34 | 200 mg | 3 days | Placebo Example 34 | 200 mg | None |
| Composition Example 35 | 200 mg | 3 days | Placebo Example 35 | 200 mg | None |
| Composition Example 36 | 200 mg | 3 days | Placebo Example 36 | 200 mg | None |
| Composition Example 37 | 200 mg | 3 days | Placebo Example 37 | 200 mg | None |
| Composition Example 38 | 200 mg | 3 days | Placebo Example 38 | 200 mg | None |
| Composition Example 39 | 200 mg | 3 days | Placebo Example 39 | 200 mg | None |
| Composition Example 40 | 200 mg | 3 days | Placebo Example 40 | 200 mg | None |
| Composition Example 41 | 200 mg | 3 days | Placebo Example 41 | 200 mg | None |
| Composition Example 42 | 200 mg | 3 days | Placebo Example 42 | 200 mg | None |
| Composition Example 43 | 200 mg | 3 days | Placebo Example 43 | 200 mg | None |
| Composition Example 44 | 200 mg | 3 days | Placebo Example 44 | 200 mg | None |
| Composition Example 45 | 200 mg | 3 days | Placebo Example 45 | 200 mg | None |
| Composition Example 46 | 200 mg | 3 days | Placebo Example 46 | 200 mg | None |
| Composition Example 47 | 200 mg | 3 days | Placebo Example 47 | 200 mg | None |
| Composition Example 48 | 200 mg | 3 days | Placebo Example 48 | 200 mg | None |
| Composition Example 49 | 200 mg | 3 days | Placebo Example 49 | 200 mg | None |
| Composition Example 50 | 200 mg | 3 days | Placebo Example 50 | 200 mg | None |
| Composition Example 51 | 200 mg | 3 days | Placebo Example 51 | 200 mg | None |
| Composition Example 52 | 200 mg | 3 days | Placebo Example 52 | 200 mg | None |
| Composition Example 53 | 200 mg | 3 days | Placebo Example 53 | 200 mg | None |
| Composition Example 54 | 50 mg | 2 days | Placebo Example 54 | 200 mg | None |
| Composition Example 55 | 200 mg | 3 days | Placebo Example 55 | 200 mg | None |
| Composition Example 56 | 200 mg | 3 days | Placebo Example 10 | 200 mg | None |

-continued

Rota Virus - RNA Non Enveloped

| Treated with the Compositions of Table C | | | Placebo of Table B | | |
|---|---|---|---|---|---|
| Composition of the present invention | Dosage | Virus free | Placebo of table B Used | Dosage | Virus free after 3 days |
| Composition Example 57 | 200 mg | 3 days | Placebo Example 10 | 200 mg | None |
| Composition Example 58 | 200 mg | 3 days | Placebo Example 10 | 200 mg | None |
| Composition Example 59 | 200 mg | 3 days | Placebo Example 10 | 200 mg | None |
| Composition Example 60 | 200 mg | 3 days | Placebo Example 10 | 200 mg | None |
| Composition Example 61 | 200 mg | 3 days | Placebo Example 10 | 200 mg | None |
| Composition Example 62 | 200 mg | 3 days | Placebo Example 10 | 200 mg | None |
| Composition Example 63 | 200 mg | 3 days | Placebo Example 10 | 200 mg | None |
| Composition Example 64 | 200 mg | 3 days | Placebo Example 10 | 200 mg | None |
| Composition Example 65 | 200 mg | 3 days | Placebo Example 10 | 200 mg | None |
| Composition Example 66 | 200 mg | 3 days | Placebo Example 10 | 200 mg | None |
| Composition Example 67 | 200 mg | 3 days | Placebo Example 10 | 200 mg | None |
| Composition Example 68 | 200 mg | 3 days | Placebo Example 10 | 200 mg | None |
| Composition Example 69 | 200 mg | 3 days | Placebo Example 10 | 200 mg | None |
| Composition Example 70 | 200 mg | 3 days | Placebo Example 10 | 200 mg | None |

DNA Enveloped Virus—Herpes Simplex Virus

An in vivo comparative test was done on human subjects experiencing recurring Cold sores on the lips caused by the Herpes I Simplex Virus.

55 human subjects were treated with a separate alternative composition from the Composition of examples 1 to 70 of the present invention (see table C). Two drops containing 2 mg of the composition was administered topically on the lips between 1 to 5 times. Within one day the Cold sore stopped developing into a lesion.

The placebo group of other human subjects was treated with 5 times two drops containing 2 mg of the Placebo compositions (see Table B). After one day the Cold sores continued to develop into lesions.

The man skilled in the art knows how to perform such tests.

Herpes Labialis - DNA - Enveloped

| Treated with the Compositions of Table C | | | Placebo of Table B | | |
|---|---|---|---|---|---|
| Composition of the present Invention | Applications | Lesion stopped | Placebo Used | Applications | Lesion stopped after one day |
| Composition Example 1 | 1 | same day | Placebo Example 1 | 5 | none |
| Composition Example 2 | 5 | next day | Placebo Example 2 | 5 | none |
| Composition Example 3 | 5 | next day | Placebo Example 3 | 5 | none |
| Composition Example 4 | 5 | next day | Placebo Example 4 | 5 | none |
| Composition Example 5 | 5 | next day | Placebo Example 5 | 5 | none |
| Composition Example 6 | 5 | next day | Placebo Example 6 | 5 | none |
| Composition Example 7 | 5 | next day | | | |
| Composition Example 8 | 5 | next day | Placebo Example 8 | 5 | none |
| Composition Example 9 | 5 | next day | Placebo Example 9 | 5 | none |
| Composition Example 10 | 5 | next day | Placebo Example 10 | 5 | none |
| Composition Example 11 | 5 | next day | Placebo Example 11 | 5 | none |
| Composition Example 12 | 5 | next day | Placebo Example 12 | 5 | none |
| Composition Example 13 | 5 | next day | Placebo Example 13 | 5 | none |
| Composition Example 14 | 5 | next day | Placebo Example 14 | 5 | none |
| Composition Example 15 | 5 | next day | Placebo Example 15 | 5 | none |
| Composition Example 16 | 5 | next day | Placebo Example 16 | 5 | none |
| Composition Example 17 | 5 | next day | Placebo Example 17 | 5 | none |
| Composition Example 18 | 5 | next day | Placebo Example 18 | 5 | none |
| Composition Example 19 | 5 | next day | Placebo Example 19 | 5 | none |
| Composition Example 20 | 5 | next day | Placebo Example 20 | 5 | none |
| Composition Example 21 | 5 | next day | Placebo Example 21 | 5 | none |
| Composition Example 22 | 5 | next day | Placebo Example 22 | 5 | none |
| Composition Example 23 | 5 | next day | Placebo Example 23 | 5 | none |
| Composition Example 24 | 5 | next day | Placebo Example 24 | 5 | none |
| Composition Example 25 | 5 | next day | Placebo Example 25 | 5 | none |
| Composition Example 26 | 5 | next day | Placebo Example 26 | 5 | none |

| Herpes Labialis - DNA - Enveloped ||||||
|---|---|---|---|---|---|
| Treated with the Compositions of Table C ||| Placebo of Table B |||
| Composition of the present Invention | Applications | Lesion stopped | Placebo Used | Applications | Lesion stopped after one day |
| Composition Example 27 | 5 | next day | Placebo Example 27 | 5 | none |
| Composition Example 28 | 5 | next day | Placebo Example 28 | 5 | none |
| Composition Example 29 | 5 | next day | Placebo Example 29 | 5 | none |
| Composition Example 30 | 5 | next day | Placebo Example 30 | 5 | none |
| Composition Example 31 | 5 | next day | Placebo Example 31 | 5 | none |
| Composition Example 32 | 5 | next day | Placebo Example 32 | 5 | none |
| Composition Example 33 | 5 | next day | Placebo Example 33 | 5 | none |
| Composition Example 34 | 5 | next day | Placebo Example 34 | 5 | none |
| Composition Example 35 | 5 | next day | Placebo Example 35 | 5 | none |
| Composition Example 36 | 5 | next day | Placebo Example 36 | 5 | none |
| Composition Example 37 | 5 | next day | Placebo Example 37 | 5 | none |
| Composition Example 38 | 5 | next day | Placebo Example 38 | 5 | none |
| Composition Example 39 | 5 | next day | Placebo Example 39 | 5 | none |
| Composition Example 40 | 5 | next day | Placebo Example 40 | 5 | none |
| Composition Example 41 | 5 | next day | Placebo Example 41 | 5 | none |
| Composition Example 42 | 5 | next day | Placebo Example 42 | 5 | none |
| Composition Example 43 | 5 | next day | Placebo Example 43 | 5 | none |
| Composition Example 44 | 5 | next day | Placebo Example 44 | 5 | none |
| Composition Example 45 | 5 | next day | Placebo Example 45 | 5 | none |
| Composition Example 46 | 5 | next day | Placebo Example 46 | 5 | none |
| Composition Example 47 | 5 | next day | Placebo Example 47 | 5 | none |
| Composition Example 48 | 5 | next day | Placebo Example 48 | 5 | none |
| Composition Example 49 | 5 | next day | Placebo Example 49 | 5 | none |
| Composition Example 50 | 5 | next day | Placebo Example 50 | 5 | none |
| Composition Example 51 | 5 | next day | Placebo Example 51 | 5 | none |
| Composition Example 52 | 5 | next day | Placebo Example 52 | 5 | none |
| Composition Example 53 | 3 | same day | Placebo Example 53 | 5 | none |
| Composition Example 54 | 1 | same day | Placebo Example 54 | 5 | none |
| Composition Example 55 | 5 | next day | Placebo Example 55 | 5 | none |
| Composition Example 56 | 5 | next day | Placebo Example 10 | 5 | none |
| Composition Example 57 | 5 | next day | Placebo Example 10 | 5 | none |
| Composition Example 58 | 5 | next day | Placebo Example 10 | 5 | none |
| Composition Example 59 | 5 | next day | Placebo Example 10 | 5 | none |
| Composition Example 60 | 5 | next day | Placebo Example 10 | 5 | none |
| Composition Example 61 | 5 | next day | Placebo Example 10 | 5 | none |
| Composition Example 62 | 5 | next day | Placebo Example 10 | 5 | none |
| Composition Example 63 | 5 | next day | Placebo Example 10 | 5 | none |
| Composition Example 64 | 5 | next day | Placebo Example 10 | 5 | none |
| Composition Example 65 | 5 | next day | Placebo Example 10 | 5 | none |
| Composition Example 66 | 5 | next day | Placebo Example 10 | 5 | none |
| Composition Example 67 | 5 | next day | Placebo Example 10 | 5 | none |
| Composition Example 68 | 5 | next day | Placebo Example 10 | 5 | none |
| Composition Example 69 | 5 | next day | Placebo Example 10 | 5 | none |
| Composition Example 70 | 5 | next day | Placebo Example 10 | 5 | none |

DNA Non-enveloped Virus—Papilloma Virus:

An in vivo comparative test on Skin Warts caused by the Human Papilloma Virus was performed on human subjects who had at least one or more skin warts on the hands, arms or other parts of the body.

55 human subjects were treated a separate alternative composition from the composition Examples list of table C (compositions Examples 1-70). One drop containing (2 mg) of the composition was administered topically on the wart between 3 times for one day up to five times a day for 14 days (i.e. 70 applications). Viral deactivation was confirmed as soon as the wart started to feel soft. This occurred generally between 6 to 21 days. The wart started to disappear and generally was invisible within 30 to 45 days form the start of the study.

The placebo group of other human subjects applied one drop containing 2 mg of the placebo 5 times a day for 14 days (70 applications) see the compositions of table B. None of the Placebo subjects experience any softening of the warts and none of the warts disappeared even partly within 45 days.

The man skilled in the art knows how to perform such tests.

| Papilloma warts - DNA Non Enveloped | | | | | |
|---|---|---|---|---|---|
| Treated with the Compositions of Table C | | | Placebo of Table B | | |
| Composition of the present invention | Applications | Wart free | Placebo of table B Used | Applications | Wart free after 45 days |
| Composition Example 1 | 9 | 30 days | Placebo Example 1 | 70 | None |
| Composition Example 2 | 70 | 45 days | Placebo Example 2 | 70 | None |
| Composition Example 3 | 70 | 45 days | Placebo Example 3 | 70 | None |
| Composition Example 4 | 70 | 45 days | Placebo Example 4 | 70 | None |
| Composition Example 5 | 70 | 45 days | Placebo Example 5 | 70 | None |
| Composition Example 6 | 70 | 45 days | Placebo Example 6 | 70 | None |
| Composition Example 7 | 70 | 45 days | | | |
| Composition Example 8 | 70 | 45 days | Placebo Example 8 | 70 | None |
| Composition Example 9 | 70 | 45 days | Placebo Example 9 | 70 | None |
| Composition Example 10 | 70 | 45 days | Placebo Example 10 | 70 | None |
| Composition Example 11 | 70 | 45 days | Placebo Example 11 | 70 | None |
| Composition Example 12 | 70 | 45 days | Placebo Example 12 | 70 | None |
| Composition Example 13 | 70 | 45 days | Placebo Example 13 | 70 | None |
| Composition Example 14 | 70 | 45 days | Placebo Example 14 | 70 | None |
| Composition Example 15 | 70 | 45 days | Placebo Example 15 | 70 | None |
| Composition Example 16 | 70 | 45 days | Placebo Example 16 | 70 | None |
| Composition Example 17 | 70 | 45 days | Placebo Example 17 | 70 | None |
| Composition Example 18 | 70 | 45 days | Placebo Example 18 | 70 | None |
| Composition Example 19 | 70 | 45 days | Placebo Example 19 | 70 | None |
| Composition Example 20 | 70 | 45 days | Placebo Example 20 | 70 | None |
| Composition Example 21 | 70 | 45 days | Placebo Example 21 | 70 | None |
| Composition Example 22 | 70 | 45 days | Placebo Example 22 | 70 | None |
| Composition Example 23 | 70 | 45 days | Placebo Example 23 | 70 | None |
| Composition Example 24 | 70 | 45 days | Placebo Example 24 | 70 | None |
| Composition Example 25 | 70 | 45 days | Placebo Example 25 | 70 | None |
| Composition Example 26 | 70 | 45 days | Placebo Example 26 | 70 | None |
| Composition Example 27 | 70 | 45 days | Placebo Example 27 | 70 | None |
| Composition Example 28 | 70 | 45 days | Placebo Example 28 | 70 | None |
| Composition Example 29 | 70 | 45 days | Placebo Example 29 | 70 | None |
| Composition Example 30 | 70 | 45 days | Placebo Example 30 | 70 | None |
| Composition Example 31 | 70 | 45 days | Placebo Example 31 | 70 | None |
| Composition Example 32 | 70 | 45 days | Placebo Example 32 | 70 | None |
| Composition Example 33 | 70 | 45 days | Placebo Example 33 | 70 | None |
| Composition Example 34 | 70 | 45 days | Placebo Example 34 | 70 | None |
| Composition Example 35 | 70 | 45 days | Placebo Example 35 | 70 | None |
| Composition Example 36 | 70 | 45 days | Placebo Example 36 | 70 | None |
| Composition Example 37 | 70 | 45 days | Placebo Example 37 | 70 | None |
| Composition Example 38 | 70 | 45 days | Placebo Example 38 | 70 | None |
| Composition Example 39 | 70 | 45 days | Placebo Example 39 | 70 | None |
| Composition Example 40 | 70 | 45 days | Placebo Example 40 | 70 | None |
| Composition Example 41 | 70 | 45 days | Placebo Example 41 | 70 | None |
| Composition Example 42 | 70 | 45 days | Placebo Example 42 | 70 | None |
| Composition Example 43 | 70 | 45 days | Placebo Example 43 | 70 | None |

Papilloma warts - DNA Non Enveloped

| Treated with the Compositions of Table C | | | Placebo of Table B | | |
|---|---|---|---|---|---|
| Composition of the present invention | Applications | Wart free | Placebo of table B Used | Applications | Wart free after 45 days |
| Composition Example 44 | 70 | 45 days | Placebo Example 44 | 70 | None |
| Composition Example 45 | 70 | 45 days | Placebo Example 45 | 70 | None |
| Composition Example 46 | 70 | 45 days | Placebo Example 46 | 70 | None |
| Composition Example 47 | 70 | 45 days | Placebo Example 47 | 70 | None |
| Composition Example 48 | 70 | 45 days | Placebo Example 48 | 70 | None |
| Composition Example 49 | 70 | 45 days | Placebo Example 49 | 70 | None |
| Composition Example 50 | 70 | 45 days | Placebo Example 50 | 70 | None |
| Composition Example 51 | 70 | 45 days | Placebo Example 51 | 70 | None |
| Composition Example 52 | 70 | 45 days | Placebo Example 52 | 70 | None |
| Composition Example 53 | 9 | 30 days | Placebo Example 53 | 70 | None |
| Composition Example 54 | 3 | 30 days | Placebo Example 54 | 70 | None |
| Composition Example 55 | 70 | 45 days | Placebo Example 55 | 70 | None |
| Composition Example 56 | 70 | 45 days | Placebo Example 10 | 70 | None |
| Composition Example 57 | 70 | 45 days | Placebo Example 10 | 70 | None |
| Composition Example 58 | 70 | 45 days | Placebo Example 10 | 70 | None |
| Composition Example 59 | 70 | 45 days | Placebo Example 10 | 70 | None |
| Composition Example 60 | 70 | 45 days | Placebo Example 10 | 70 | None |
| Composition Example 61 | 70 | 45 days | Placebo Example 10 | 70 | None |
| Composition Example 62 | 70 | 45 days | Placebo Example 10 | 70 | None |
| Composition Example 63 | 70 | 45 days | Placebo Example 10 | 70 | None |
| Composition Example 64 | 70 | 45 days | Placebo Example 10 | 70 | None |
| Composition Example 65 | 70 | 45 days | Placebo Example 10 | 70 | None |
| Composition Example 66 | 70 | 45 days | Placebo Example 10 | 70 | None |
| Composition Example 67 | 70 | 45 days | Placebo Example 10 | 70 | None |
| Composition Example 68 | 70 | 45 days | Placebo Example 10 | 70 | None |
| Composition Example 69 | 70 | 45 days | Placebo Example 10 | 70 | None |
| Composition Example 70 | 70 | 45 days | Placebo Example 10 | 70 | None |

General Conclusion:

The comparative tests clearly prove that the 70 compositions of Table C of the present invention provide unexpected and surprising results in vivo. The synergistic combination of components of examples 1 to 70 provide an unexpected and surprising therapeutical effect.

The invention claimed is:

1. An antiviral composition, comprising:
   a pharmaceutically acceptable carrier suitable for oral or parenteral use in admixture with
   a synergistic combination of (−)-Carvone, (+)-Carvone, Trans-Geraniol, and at least one more component selected from the group consisting of Eugenol methylether, Linalooloxide, (cis+trans)-1,2-(+)-Limonene oxide, (+/−)-Isomenthol, Eugenol, Trans-Nerolidol, (cis+trans)-Nerolidol, and Lavendulol;
   wherein the synergistic combination comprises between 10 and 35 wt % (−)-Carvone, between 10 and 35 wt % (+)-Carvone, between 10 and 35 wt % Trans-Geraniol, and at least 0.5 wt % of the at least one more component and is synergistic with respect to an antiviral effect of the (−)-Carvone, (+)-Carvone, trans-geraniol, and the at least one more component;
   and
   wherein the (−)-Carvone and (+)-Carvone, the trans-Geraniol, and the at least one more component are present in the composition in an amount effective for treatment of a disease caused by at least one of a Herpes Virus, a Rotavirus, a Porcine Reproductive and Respiratory Syndrome virus, and a Papilloma virus.

2. The antiviral composition of claim 1 wherein the antiviral composition is formulated for oral, nasal, pulmonary, or parenteral administration.

3. The antiviral composition of claim 1 wherein the antiviral composition is formulated as a disinfectant.

4. The antiviral composition of claim 1 wherein the antiviral composition is formulated for ex vivo use as viral inhibitor.

5. An antiviral composition comprising a pharmaceutically acceptable carrier suitable for oral or parenteral use in admixture with a synergistic and antivirally effective combination of (−)-Carvone and (+)-Carvone and Trans-Geraniol and (Cis+Trans)-Nerolidol and Eugenol, wherein the (−)-Carvone and (+)-Carvone are each present in an amount of between 10-35 wt %, the Trans-Geraniol is present in an amount of between 10-35 wt %, wherein each of the (−)-Carvone and (+)-Carvone and Trans-Geraniol and (Cis+Trans)-Nerolidol and Eugenol, wherein the (Cis+Trans)-Nerolidol and Eugenol are each present in an amount of at least 0.5 wt %, and wherein the synergistic combination is synergistic with respect to the antiviral effect of the combination against at least one of a Herpes Virus, a Rotavirus, a Porcine Reproductive and Respiratory Syndrome virus, and a Papilloma virus.

* * * * *